(12) United States Patent
Brauker et al.

(10) Patent No.: US 7,192,450 B2
(45) Date of Patent: *Mar. 20, 2007

(54) POROUS MEMBRANES FOR USE WITH IMPLANTABLE DEVICES

(75) Inventors: James H. Brauker, San Diego, CA (US); Victoria Carr-Brendel, Pleasanton, CA (US); Mark A. Tapsak, Orangeville, PA (US)

(73) Assignee: DexCom, Inc., San Diego, CA (US)

( * ) Notice: Subject to any disclaimer, the term of this patent is extended or adjusted under 35 U.S.C. 154(b) by 579 days.

This patent is subject to a terminal disclaimer.

(21) Appl. No.: 10/647,065

(22) Filed: Aug. 22, 2003

(65) Prior Publication Data

US 2005/0112169 A1 May 26, 2005

Related U.S. Application Data

(60) Provisional application No. 60/472,673, filed on May 21, 2003.

(51) Int. Cl.
*A61F 2/02* (2006.01)
(52) U.S. Cl. .................................. 623/23.76
(58) Field of Classification Search ............ 623/23.76, 623/23.72; 424/424
See application file for complete search history.

(56) References Cited

U.S. PATENT DOCUMENTS

| | | | |
|---|---|---|---|
| 3,775,182 A | 11/1973 | Patton et al. | |
| 3,929,971 A | 12/1975 | Roy | 423/308 |
| 3,964,974 A | 6/1976 | Banauch et al. | |
| 3,966,580 A | 6/1976 | Janata et al. | 204/403.07 |
| 3,979,274 A | 9/1976 | Newman | 204/403.09 |
| 4,024,312 A | 5/1977 | Korpman | |
| 4,040,908 A | 8/1977 | Clark, Jr. | 205/778 |
| 4,073,713 A | 2/1978 | Newman | 204/403.9 |
| 4,076,656 A | 2/1978 | White et al. | 521/64 |
| 4,172,770 A | 10/1979 | Semersky et al. | 205/778 |
| 4,197,840 A | 4/1980 | Beck et al. | |
| 4,215,703 A | 8/1980 | Willson | |
| 4,240,889 A | 12/1980 | Yoda et al. | 204/403.09 |
| 4,255,500 A | 3/1981 | Hooke | |
| 4,259,540 A | 3/1981 | Sabia | |
| 4,353,888 A | 10/1982 | Sefton | 424/424 |
| 4,374,013 A | 2/1983 | Enfors | |
| 4,388,166 A | 6/1983 | Suzuki et al. | 204/403.05 |
| 4,415,666 A | 11/1983 | D'Orazio et al. | 204/403.11 |
| 4,418,148 A | 11/1983 | Oberhardt | 204/403.11 |
| 4,431,004 A | 2/1984 | Bessman et al. | 600/347 |
| 4,436,094 A | 3/1984 | Cerami | 600/347 |
| 4,484,987 A | 11/1984 | Gough | 205/778 |
| 4,506,680 A | 3/1985 | Stokes | 607/120 |
| 4,534,355 A | 8/1985 | Potter | 600/360 |
| 4,577,642 A | 3/1986 | Stokes | 607/120 |
| 4,650,547 A | 3/1987 | Gough | 205/778 |
| 4,663,824 A | 5/1987 | Kenmochi | |
| 4,671,288 A | 6/1987 | Gough | 600/347 |
| 4,686,044 A | 8/1987 | Behnke et al. | 210/500.22 |
| 4,689,309 A | 8/1987 | Jones | 436/95 |
| 4,702,732 A | 10/1987 | Powers et al. | 604/20 |
| 4,703,756 A | 11/1987 | Gough et al. | 600/347 |
| 4,711,251 A | 12/1987 | Stokes | 607/116 |
| 4,753,652 A | 6/1988 | Langer et al. | 623/1.42 |
| 4,757,022 A | 7/1988 | Shults et al. | 204/403.05 |
| 4,759,828 A | 7/1988 | Young et al. | 205/778 |
| 4,776,944 A | 10/1988 | Janata et al. | 204/403.08 |
| 4,781,798 A | 11/1988 | Gough | 205/783 |
| 4,803,243 A | 2/1989 | Fujimoto et al. | 525/100 |
| 4,810,470 A | 3/1989 | Burkhardt et al. | 422/56 |
| 4,861,830 A | 8/1989 | Ward, Jr. | 525/92 A |
| 4,871,440 A | 10/1989 | Nagata et al. | |
| 4,889,744 A | 12/1989 | Quaid | 427/2.24 |
| 4,890,620 A | 1/1990 | Gough | 600/348 |
| 4,927,407 A | 5/1990 | Dorman | |
| 4,935,345 A | 6/1990 | Guilbeau et al. | 435/14 |

(Continued)

FOREIGN PATENT DOCUMENTS

EP 0107634 5/1984

(Continued)

OTHER PUBLICATIONS

PCT International Search Report for PCT International Application No. PCT/US2004/015909 mailed Dec. 21, 2004.

(Continued)

*Primary Examiner*—Sandra E. Saucier
*Assistant Examiner*—Satyendra K. Singh
(74) *Attorney, Agent, or Firm*—Knobbe Martens Olson & Bear LLP

(57) ABSTRACT

A membrane for implantation in soft tissue comprising a first domain that supports tissue ingrowth, disrupts contractile forces typically found in a foreign body response, encourages vascularity, and interferes with barrier cell layer formation, and a second domain that is resistant to cellular attachment, is impermeable to cells and cell processes, and allows the passage of analytes. The membrane allows for long-term analyte transport in vivo and is suitable for use as a biointerface for implantable analyte sensors, cell transplantation devices, drug delivery devices, and/or electrical signal delivering or measuring devices. The membrane architecture, including cavity size, depth, and interconnectivity, provide long-term robust functionality of the membrane in vivo.

28 Claims, 13 Drawing Sheets

U.S. PATENT DOCUMENTS

| | | | |
|---|---|---|---|
| 4,963,595 A | 10/1990 | Ward et al. | 525/415 |
| 4,984,929 A | 1/1991 | Rock et al. | 403/230 |
| 4,986,671 A | 1/1991 | Sun et al. | 374/131 |
| 4,994,167 A | 2/1991 | Shults et al. | 204/403.05 |
| 5,002,572 A | 3/1991 | Picha | 623/23.74 |
| 5,007,929 A | 4/1991 | Quaid | 623/8 |
| 5,059,654 A | 10/1991 | Hou et al. | 525/54.1 |
| 5,067,491 A | 11/1991 | Taylor et al. | |
| 5,101,814 A | 4/1992 | Palti | 600/347 |
| 5,113,871 A | 5/1992 | Viljanto et al. | 600/581 |
| 5,165,407 A | 11/1992 | Wilson et al. | 600/345 |
| 5,171,689 A | 12/1992 | Kawaguri et al. | |
| 5,190,041 A | 3/1993 | Palti | 600/347 |
| 5,235,003 A | 8/1993 | Ward et al. | 525/476 |
| 5,271,736 A | 12/1993 | Picha | 623/23.74 |
| 5,282,848 A | 2/1994 | Schmitt | |
| 5,285,513 A | 2/1994 | Kaufman et al. | |
| 5,304,468 A | 4/1994 | Phillips et al. | |
| 5,310,469 A | 5/1994 | Cunningham et al. | |
| 5,314,471 A | 5/1994 | Brauker et al. | 623/23.72 |
| 5,322,063 A | 6/1994 | Allen et al. | 600/347 |
| 5,326,356 A | 7/1994 | Della Valle et al. | 623/15.12 |
| 5,330,521 A | 7/1994 | Cohen | |
| 5,340,352 A | 8/1994 | Nakanishi et al. | 450/57 |
| 5,342,409 A | 8/1994 | Mullett | |
| 5,343,869 A | 9/1994 | Pross et al. | |
| 5,344,454 A | 9/1994 | Clarke et al. | 623/23.72 |
| 5,348,788 A | 9/1994 | White | 428/131 |
| 5,356,786 A | 10/1994 | Heller et al. | 205/778 |
| 5,372,133 A | 12/1994 | Hogen Esch | 600/377 |
| 5,380,536 A | 1/1995 | Hubbell et al. | 424/497 |
| 5,384,028 A | 1/1995 | Ito | |
| 5,390,671 A | 2/1995 | Lord et al. | |
| 5,391,250 A | 2/1995 | Cheney et al. | 156/268 |
| 5,397,848 A | 3/1995 | Yang et al. | 525/477 |
| 5,411,647 A | 5/1995 | Johnson et al. | |
| 5,428,123 A | 6/1995 | Ward et al. | 528/28 |
| 5,431,160 A | 7/1995 | Wilkins | 600/347 |
| 5,453,278 A | 9/1995 | Chan et al. | 424/422 |
| 5,462,064 A | 10/1995 | D'Angelo et al. | 600/584 |
| 5,469,846 A | 11/1995 | Khan | 600/347 |
| 5,476,094 A | 12/1995 | Allen et al. | 600/342 |
| 5,484,404 A | 1/1996 | Schulman et al. | |
| 5,491,474 A | 2/1996 | Suni et al. | |
| 5,496,453 A | 3/1996 | Uenoyama et al. | 205/777.5 |
| 5,531,878 A | 7/1996 | Vadgama et al. | 205/778 |
| 5,540,828 A | 7/1996 | Yacynych | 205/198 |
| 5,545,220 A | 8/1996 | Andrews et al. | 623/8 |
| 5,545,223 A | 8/1996 | Neuenfeldt et al. | 435/325 |
| 5,549,675 A | 8/1996 | Neuenfeldt et al. | 435/325 |
| 5,564,439 A | 10/1996 | Picha | 604/890.1 |
| 5,568,806 A | 10/1996 | Cheney et al. | |
| 5,569,186 A | 10/1996 | Lord et al. | 604/67 |
| 5,569,462 A | 10/1996 | Martinson et al. | 424/424 |
| 5,571,395 A | 11/1996 | Park et al. | |
| 5,575,930 A | 11/1996 | Tietje-Girault et al. | |
| 5,584,876 A | 12/1996 | Bruchman et al. | |
| 5,586,553 A | 12/1996 | Halili et al. | |
| 5,589,563 A | 12/1996 | Ward et al. | 528/44 |
| 5,590,651 A | 1/1997 | Shaffer et al. | |
| 5,593,440 A | 1/1997 | Brauker et al. | 424/423 |
| 5,593,852 A | 1/1997 | Heller et al. | 435/14 |
| 5,624,537 A | 4/1997 | Turner et al. | |
| 5,628,890 A | 5/1997 | Carter et al. | 204/403.05 |
| 5,653,756 A | 8/1997 | Clarke et al. | 623/11.11 |
| 5,653,863 A | 8/1997 | Genshaw et al. | 205/777.5 |
| 5,658,330 A | 8/1997 | Carlisle et al. | 623/11.11 |
| 5,660,163 A | 8/1997 | Schulman et al. | |
| 5,683,562 A | 11/1997 | Schaffar et al. | |
| 5,686,829 A | 11/1997 | Girault | |
| 5,706,807 A | 1/1998 | Picha | 600/345 |
| 5,711,861 A | 1/1998 | Ward et al. | 600/347 |
| 5,713,888 A | 2/1998 | Neuenfeldt et al. | 604/891.1 |
| 5,733,336 A | 3/1998 | Neuenfeldt et al. | 435/325 |
| 5,741,330 A | 4/1998 | Brauker et al. | |
| 5,756,632 A | 5/1998 | Ward et al. | 528/28 |
| 5,776,324 A | 7/1998 | Usala | 600/345 |
| 5,777,060 A | 7/1998 | Van Antwerp | 528/28 |
| 5,779,665 A | 7/1998 | Mastrototaro et al. | |
| 5,782,912 A | 7/1998 | Brauker et al. | 424/422 |
| 5,783,054 A | 7/1998 | Raguse et al. | 204/403.08 |
| 5,787,900 A | 8/1998 | Butler et al. | |
| 5,791,344 A | 8/1998 | Schulman et al. | 600/347 |
| 5,795,774 A | 8/1998 | Matsumoto et al. | 204/403.11 |
| 5,798,065 A | 8/1998 | Picha | 264/46.4 |
| 5,800,529 A | 9/1998 | Brauker et al. | 623/2.38 |
| 5,807,406 A | 9/1998 | Brauker et al. | 424/423 |
| 5,811,487 A | 9/1998 | Schulz, Jr. et al. | 524/862 |
| 5,833,603 A | 11/1998 | Kovacs et al. | |
| 5,837,728 A | 11/1998 | Purcell | |
| 5,840,240 A | 11/1998 | Stenoien et al. | 264/425 |
| 5,851,197 A | 12/1998 | Marano et al. | |
| 5,861,019 A | 1/1999 | Sun et al. | 607/60 |
| 5,871,514 A | 2/1999 | Wiklund et al. | 607/36 |
| 5,882,494 A | 3/1999 | Van Antwerp | 600/347 |
| 5,897,578 A | 4/1999 | Wiklund et al. | 607/36 |
| 5,904,708 A | 5/1999 | Goedeke | 607/18 |
| 5,910,554 A | 6/1999 | Kempe et al. | 526/320 |
| 5,913,998 A | 6/1999 | Butler et al. | 156/245 |
| 5,914,026 A | 6/1999 | Blubaugh, Jr. et al. | 600/347 |
| 5,917,346 A | 6/1999 | Gord | |
| 5,919,215 A | 7/1999 | Wiklund et al. | 607/36 |
| 5,931,814 A | 8/1999 | Alex et al. | |
| 5,957,903 A | 9/1999 | Mirzaee et al. | |
| 5,964,261 A | 10/1999 | Neuenfeldt et al. | 141/327 |
| 5,964,804 A | 10/1999 | Brauker et al. | 424/423 |
| 5,964,993 A | 10/1999 | Blubaugh et al. | |
| 5,965,380 A | 10/1999 | Heller et al. | 435/14 |
| 5,976,085 A | 11/1999 | Kimball et al. | 600/309 |
| 5,985,129 A | 11/1999 | Gough et al. | 205/724 |
| 5,999,848 A | 12/1999 | Gord et al. | 607/2 |
| 6,001,067 A | 12/1999 | Shults et al. | 600/584 |
| 6,001,471 A | 12/1999 | Bries et al. | |
| 6,011,984 A | 1/2000 | Van Antwerp et al. | |
| 6,013,113 A | 1/2000 | Mika | |
| 6,016,448 A | 1/2000 | Busacker et al. | 607/29 |
| 6,049,727 A | 4/2000 | Crothall | |
| 6,063,637 A | 5/2000 | Arnold et al. | |
| 6,081,736 A | 6/2000 | Colvin et al. | 600/377 |
| 6,083,710 A | 7/2000 | Heller et al. | 600/347 |
| 6,088,608 A | 7/2000 | Schulman et al. | 600/345 |
| 6,093,172 A | 7/2000 | Funderburk et al. | |
| 6,103,033 A | 8/2000 | Say et al. | |
| 6,115,634 A | 9/2000 | Donders et al. | |
| 6,119,028 A | 9/2000 | Schulman et al. | 600/345 |
| 6,121,009 A | 9/2000 | Heller et al. | |
| 6,134,461 A | 10/2000 | Say et al. | |
| 6,135,978 A | 10/2000 | Houben et al. | 604/66 |
| 6,144,869 A | 11/2000 | Berner et al. | 600/347 |
| 6,162,611 A | 12/2000 | Heller et al. | 435/14 |
| 6,167,614 B1 | 1/2001 | Tuttle et al. | |
| 6,175,752 B1 | 1/2001 | Say et al. | 600/345 |
| 6,187,062 B1 | 2/2001 | Oweis et al. | |
| 6,189,536 B1 | 2/2001 | Martinez et al. | |
| 6,200,772 B1 | 3/2001 | Vadgama et al. | 435/25 |
| 6,201,980 B1 | 3/2001 | Darrow et al. | 600/347 |
| 6,206,856 B1 | 3/2001 | Mahurkar | |
| 6,208,894 B1 | 3/2001 | Schulman et al. | 607/2 |
| 6,212,416 B1 | 4/2001 | Ward et al. | 600/345 |
| 6,214,185 B1 | 4/2001 | Offenbacher et al. | |
| 6,230,059 B1 | 5/2001 | Duffin | 607/60 |
| 6,231,879 B1 | 5/2001 | Li et al. | 424/422 |
| 6,233,471 B1 | 5/2001 | Berner et al. | 600/345 |
| 6,241,863 B1 | 6/2001 | Monbouquette | 205/777.5 |

| | | | | | |
|---|---|---|---|---|---|
| 6,248,067 B1 | 6/2001 | Causey, III et al. ........ 600/365 | 2002/0193885 A1 | 12/2002 | Legeay et al. |
| 6,256,522 B1 | 7/2001 | Schultz ....................... 600/317 | 2003/0006669 A1 | 1/2003 | Pei et al. |
| 6,259,937 B1 | 7/2001 | Schulman et al. .......... 600/345 | 2003/0023317 A1 | 1/2003 | Shults et al. |
| 6,274,285 B1 | 8/2001 | Gries et al. ................. 430/162 | 2003/0032874 A1 | 2/2003 | Rhodes et al. |
| 6,275,717 B1 | 8/2001 | Gross et al. | 2003/0036803 A1 | 2/2003 | McGhan et al. |
| 6,284,478 B1 | 9/2001 | Heller et al. .................. 435/14 | 2003/0070548 A1 | 4/2003 | Clausen |
| 6,293,925 B1 | 9/2001 | Safabash et al. | 2003/0076082 A1 | 4/2003 | Morgan et al. |
| 6,299,578 B1 | 10/2001 | Kurnik et al. .............. 600/309 | 2003/0078481 A1 | 4/2003 | McIvor et al. |
| 6,300,002 B1 | 10/2001 | Webb et al. | 2003/0078560 A1 | 4/2003 | Miller et al. |
| 6,309,351 B1 | 10/2001 | Kurnik et al. .............. 600/309 | 2003/0091433 A1 | 5/2003 | Tam et al. |
| 6,309,384 B1 | 10/2001 | Harrington et al. ........... 606/28 | 2003/0125613 A1 | 7/2003 | Enegren et al. |
| 6,325,978 B1 | 12/2001 | Labuda et al. ................. 422/84 | 2003/0188427 A1 | 10/2003 | Say et al. |
| 6,325,979 B1 | 12/2001 | Hahn et al. | 2003/0199744 A1 | 10/2003 | Buse et al. |
| 6,329,161 B1 | 12/2001 | Heller et al. .................. 435/14 | 2003/0217966 A1 | 11/2003 | Tapsak et al. |
| 6,330,464 B1 | 12/2001 | Colvin et al. | 2004/0010207 A1 | 1/2004 | Flaherty et al. |
| 6,365,670 B1 | 4/2002 | Fry ........................... 524/862 | 2004/0011671 A1 | 1/2004 | Shults et al. |
| 6,368,274 B1 | 4/2002 | Van Antwerp et al. | 2004/0015134 A1 | 1/2004 | Lavi et al. |
| 6,372,244 B1 | 4/2002 | Antanavich et al. ........ 424/423 | 2004/0030285 A1 | 2/2004 | Lavi et al. |
| 6,400,974 B1 | 6/2002 | Lesho | 2004/0030294 A1 | 2/2004 | Mahurker |
| 6,405,066 B1 | 6/2002 | Essenpreis et al. | 2004/0039406 A1 | 2/2004 | Jessen |
| 6,406,066 B1 | 6/2002 | Uegane | 2004/0045879 A1 | 3/2004 | Shults et al. |
| 6,409,674 B1 | 6/2002 | Brockway et al. | 2004/0068230 A1 | 4/2004 | Estes et al. |
| 6,413,393 B1 | 7/2002 | Van Antwerp et al. | 2004/0106857 A1 | 6/2004 | Gough |
| 6,424,847 B1 | 7/2002 | Mastrototaro et al. | 2004/0186362 A1 | 9/2004 | Brauker et al. |
| 6,447,448 B1 | 9/2002 | Ishikawa et al. | 2004/0186365 A1 | 9/2004 | Jin et al. |
| 6,447,542 B1 | 9/2002 | Weadock | 2004/0199059 A1 | 10/2004 | Brauker et al. |
| 6,454,710 B1 | 9/2002 | Ballerstadt et al. | 2004/0219664 A1 | 11/2004 | Heller et al. |
| 6,459,917 B1 | 10/2002 | Gowda et al. | | | |
| 6,461,496 B1 | 10/2002 | Feldman et al. | | FOREIGN PATENT DOCUMENTS | |
| 6,466,810 B1 | 10/2002 | Ward et al. | EP | 0 534 074 | 3/1993 |
| 6,471,689 B1 | 10/2002 | Joseph et al. | EP | 0535898 | 4/1993 |
| 6,475,750 B1 | 11/2002 | Han et al. | EP | 776628 A2 | 6/1997 |
| 6,477,392 B1 | 11/2002 | Honigs et al. | EP | 0885932 | 12/1998 |
| 6,477,395 B2 | 11/2002 | Schulman et al. | EP | 0817809 | 7/2002 |
| 6,481,440 B2 | 11/2002 | Gielen et al. | FR | 2 656 423 | 6/1991 |
| 6,498,043 B1 | 12/2002 | Schulman et al. | FR | 2760962 | 9/1998 |
| 6,514,718 B2 | 2/2003 | Heller et al. .................. 435/14 | GB | 1442303 | 7/1976 |
| 6,520,997 B1 | 2/2003 | Pekkarinen et al. | JP | 62083849 | 4/1987 |
| 6,527,729 B1 | 3/2003 | Turcott | WO | WO 90/00738 | 1/1990 |
| 6,537,318 B1 | 3/2003 | Ita et al. | WO | WO 92/07525 | 5/1992 |
| 6,541,107 B1 | 4/2003 | Zhong et al. ............. 428/312.6 | WO | WO 92/13271 | 8/1992 |
| 6,545,085 B2 | 4/2003 | Kilgour et al. | WO | WO 93/19701 | 10/1993 |
| 6,546,268 B1 | 4/2003 | Ishikawa et al. | WO | WO 95/07109 | 3/1995 |
| 6,547,839 B2 | 4/2003 | Zhang et al. | WO | WO 96/01611 | 1/1996 |
| 6,551,496 B1 | 4/2003 | Moles et al. | WO | WO 96/30431 | 10/1996 |
| 6,558,321 B1 | 5/2003 | Burd et al. | WO | WO 96/36296 | 11/1996 |
| 6,560,471 B1 | 5/2003 | Heller et al. | WO | WO 97/43633 | 11/1997 |
| 6,569,521 B1 | 5/2003 | Sheridan et al. | WO | WO 98/24358 | 6/1998 |
| 6,579,498 B1 | 6/2003 | Eglise | WO | WO 96/32076 | 10/1998 |
| 6,585,763 B1 | 7/2003 | Keilman et al. | WO | WO 00/13003 | 3/2000 |
| 6,607,509 B2 | 8/2003 | Bobroff et al. | WO | WO0019887 | 4/2000 |
| 6,613,379 B2 | 9/2003 | Ward et al. | WO | WO 00/32098 | 6/2000 |
| 6,615,078 B1 | 9/2003 | Burson et al. | WO | WO0033065 | 6/2000 |
| 6,618,934 B1 | 9/2003 | Feldman et al. | WO | WO 00/59373 | 10/2000 |
| 6,642,015 B2 | 11/2003 | Vachon et al. | WO | WO 01/12158 | 2/2001 |
| 6,645,181 B1 | 11/2003 | Lavi et al. | WO | WO0120019 | 3/2001 |
| 6,648,821 B2 | 11/2003 | Lebel et al. | WO | WO0120334 | 3/2001 |
| 6,654,625 B1 | 11/2003 | Say et al. | WO | WO 01/43660 | 6/2001 |
| 6,683,535 B1 | 1/2004 | Utke | WO | WO 01/58348 | 8/2001 |
| 6,694,191 B2 | 2/2004 | Starkweather et al. | WO | WO 01/88524 | 11/2001 |
| 6,695,860 B1 | 2/2004 | Ward et al. | WO | WO 02/053764 | 7/2002 |
| 6,699,218 B2 | 3/2004 | Flaherty et al. | WO | WO 03101862 A1 | 12/2003 |
| 6,702,857 B2 | 3/2004 | Brauker et al. | | | |
| 6,721,587 B2 | 4/2004 | Gough | | | |
| 6,731,976 B2 | 5/2004 | Penn et al. | | | |
| 6,740,075 B2 | 5/2004 | Lebel et al. | | | |
| 6,741,877 B1 | 5/2004 | Shults et al. | | | |
| 6,810,290 B2 | 10/2004 | Lebel et al. | | | |
| 2002/0022883 A1 | 2/2002 | Burg | | | |
| 2002/0042090 A1 | 4/2002 | Heller et al. | | | |
| 2002/0133244 A1 | 9/2002 | Clara et al. | | | |
| 2002/0151796 A1 | 10/2002 | Koulik | | | |
| 2002/0182241 A1 | 12/2002 | Boerenstein et al. | | | |

OTHER PUBLICATIONS

Atanasov, et al. Biosensor for Continuous Glucose Monitoring. Biotechnology and Bioengineering 1994, 43, 262-266.

Baker, et al. Dynamic concentration challenges for biosensor characterization. Biosens Bioelectron 1993, 8, 433-441.

Bani Amer, M. M. An accurate amperometric glucose sensor based glucometer with eliminated cross-sensitivity. J Med Eng Technol 2002, 26, 208-13.

Beach, et al. Subminiature implantable potentiostat and modified commercial telemetry device for remote glucose monitoring. IEEE Transactions on Instrumentation and Measurement 1999, 48, 1239-1245.

Bindra, et al. Pulsed amperometric detection of glucose in biological fluids at a surface-modified gold electrode. Anal Chem 1989, 61, 2566-2570.

Bode, B. W. Clinical utility of the continuous glucose monitoring system. Diabetes Technol Ther 2000, 2 Suppl 1, S35-41.

Bode, et al. Continuous glucose monitoring used to adjust diabetes therapy improves glycosylated hemoglobin: a pilot study. Diabetes Res Clin Pract 1999, 46, 183-190.

Bode, et al. Using the continuous glucose monitoring system to improve the management of type 1 diabetes. Diabetes Technol Ther 2000, 2 Suppl 1, S43-8.

Bott, A. W. A Comparison of Cyclic Voltammetryand Cyclic Staircase Voltammetry. Current Separations 1997, 16:1, 23-26.

Brauker, et al. Neovascularization of synthetic membranes directed by membrane microarchitecture. J Biomed Mater Res 1995, 29, 1517-1524.

Brauker, et al. Sustained expression of high levels of human factor IX from human cells implanted within an immunoisolation device into athymic rodents. Hum Gene Ther 1998, 9, 879-888.

Brauker, J.H. Unraveling Mysteries at the Biointerface: Molecular Mediator of Inhibition of Blood Vessel Formation in the Foreign Body Capsule Revealed. Surfacts Biomaterials 2001,6, 1;5.

Bremer, et al. Benchmark data from the literature for evaluation of new glucose sensing technologies. Diabetes Technol Ther 2001,3,409-418.

Brunner, et al. Validation of home blood glucose meters with respect to clinical and analytical approaches. Diabetes Care 1998, 21, 585-590.

D'Arrigo, et al. Porous-Si based bioreactors for glucose monitoring and drugs production, Proc. of SPIE 2003, 4982, 178-184.

Dixon, et al. Characterization in vitro and in vivo of the oxygen dependence of an enzyme/polymer biosensor for monitoring brain glucose. J Neurosci Methods 2002, 119, 135-142.

Ernst, et al. Reliable glucose monitoring through the use of microsystem technology. Anal Bioanal Chem 2002, 373, 758-761.

Fare, et al. Functional characterization of a conducting polymer-based immunoassay system. Biosens Bioelectron 1998, 13, 459-470.

Frost, et al. Implantable chemical sensors for real-time clinical monitoring: progress and challenges. Curr Opin Chem Biol 2002, 6, 633-641.

Geller, et al. Use of an immunoisolation device for cell transplantation and tumor immunotherapy. Ann NY Acad Sci 1997, 831, 438-451.

Gerritsen, M. Problems associated with subcutaneously implanted glucose sensors. Diabetes Care 2000, 23, 143-5.

Gerritsen, et al. Influence of inflammatory cells and serum on the performance of implantable glucose sensors. J Biomed Mater Res 2001, 54, 69-75.

Gerritsen, et al. Performance of subcutaneously implanted glucose sensors for continuous monitoring. Neth J Med 1999, 54, 167-179.

Gilligan et al. Evaluation of a subcutaneous glucose sensor out to 3 months in a dog model. Diabetes Care 1994, 17:8, 882-887.

Gough, et al. Immobilized glucose oxidase in implantable glucose sensor technology. Diabetes Technol Ther 2000, 2, 377-380.

Gross, et al. Performance evaluation of the MiniMed continuous glucose monitoring system during patient home use. Diabetes Technol Ther 2000, 2, 49-56.

Gross, et al. Efficacy and reliability of the continuous glucose monitoring system. Diabetes Technol Ther 2000, 2 Suppl 1, S19-26.

Gross, Todd, "Letters to the Editor Re: Diabetes Technology & Therapeutics, 2000;2:49-56," vol. 3, No. 1, p. 130-131, 2001.

Hall, et al. Electrochemical oxidation of hydrogen peroxide at platinum electrodes. Part 1. An adsorption-controlled mechanism. Electrochimica Acta 1998, 43, 579-588.

Hall, et al. Electrochemical oxidation of hydrogen peroxide at platinum electrodes. Part II: effect of potential. Electrochimica Acta 1998, 43, 2015-2024.

Hall, et al. Electrochemical oxidation of hydrogen peroxide at platinum electrodes. Part III: Effect of temperature. Electrochimica Acta 1999, 44, 2455-2462.

Hall, et al. Electrochemical oxidation of hydrogen peroxide at platinum electrodes. Part IV: phosphate buffer dependence. Electrochimica Acta 1999, 44, 4573-4582.

Hall, et al. Electrochemical oxidation of hydrogen peroxide at platinum electrodes. Part V: inhibition by chloride. Electrochimica Acta 2000, 45, 3573-3579.

Hitchman, M. Measurement of Dissolved Oxygen. Chemical Analysis 1978, 49, 34-123.

Huang, C., O'Grady, W.E.; Yeager, E. Electrochemical Generation of Oxygen. 1: The Effects of Anions and Cations on Hydrogen Chemisorption and Aniodic Oxide Film Formation on Platinum Electrode. 2: The Effects of Anions and Cations on Oxygen Generation on Platinum Electrode, pp. 1-116, Aug. 1975.

Ishikawa, et al. Initial evaluation of a 290-microm diameter subcutaneous glucose sensor: glucose monitoring with a biocompatible, flexible-wire, enzyme-based amperometric microsensor in diabetic and nondiabetic humans. J Diabetes Complications 1998, 12, 295-301.

Jensen, et al. Fast Wave Forms for Pulsed Electrochemical Detection of Glucose by Incorporation of Reduction Desorption of Oxidation Products. Analytical Chemistry 1997, 69, 1776-1781.

Johnson, et al. In vivo evaluation of an electroenzymatic glucose sensor implanted in subcutaneous tissue. Biosens Bioelectron 1992, 7, 709-714.

Jovanovic, L. The role of continuous glucose monitoring in gestational diabetes mellitus. Diabetes Technol Ther 2000, 2 Suppl 1, S67-71.

Kargol, et al. Studies on the structural properties of porous membranes: measurement of linear dimensions of solutes. Biophys Chem 2001, 91, 263-271.

Kaufman, F. R. Role of the continuous glucose monitoring system in pediatric patients. Diabetes Technol Ther 2000, 2 Suppl 1, S49-52.

Kiechle, F.L. The impact of continuous glucose monitoring on hospital point-of-care testing programs. Diabetes Technol Ther 2001, 3, 647-649.

Koschinsky, et al. Sensors for glucose monitoring: technical and clinical aspects. Diabetes Metab Res Rev 2001, 17, 113-123.

Kruger, et al. Psychological motivation and patient education: a role for continuous glucose monitoring. Diabetes Technol Ther 2000, 2 Suppl 1, S93-7.

Lee, et al. Effects of pore size, void volume, and pore connectivity on tissue responses. Society for Biomaterials 1999, 25th Annual Meeting, 171.

Lerner, et al. An implantable electrochemical glucose sensor. Ann N Y Acad Sci 1984, 428, 263-278.

Leypoldt, et al. Model of a two-substrate enzyme electrode for glucose. Anal Chem 1984, 56, 2896-2904.

Makale, et al. Tissue window chamber system for validation of implanted oxygen sensors. Am J Physiol Heart Circ Physiol 2003, 284, 1-24.

Malin, et al. Noninvasive Prediction of Glucose by Near-Infrared Diffuse Reflectance Spectroscopy. Clinical Chemistry, 45:9, 1651-1658, 1999.

Maran, et al. Continuous subcutaneous glucose monitoring in diabetic patients: a multicenter analysis. Diabetes Care 2002, 25, 347-52.

Mastrototaro, J. J.; Gross, T. M., Reproducibility of the continuous glucose monitoring system matches previous reports and the intended use of the product. *Diabetes Care*, 26:256; author reply p. 257 2003.

Matsumoto, et al. A long-term lifetime amperometric glucose sensor with a perfluorocarbon polymer coating. Biosens Bioelectron 2001, 16, 271-276.

Miller, A. Human monocyte/macrophage activation and interleukin 1 generation by biomedical polymers. J Biomed Mater Res 1988, 23, 713-731.

Miller, et al. Generation of IL-1 like activity in response to biomedical polymer implants: a comparison of in vitro and in vivo models. J Biomed Mater Res 1989, 23, 1007-1026.

Miller, et al. In vitro stimulation of fibroblast activity by factors generated from human monocytes activated by biomedical polymers. Journal of J Biomed Mater Res 1989, 23, 911-930.

Moussy, et al. Biomaterials community examines biosensor biocompatibility. Diabetes Technol Ther 2000, 2, 473-477.

Mowery, et al. Preparation and characterization of hydrophobic polymeric films that are thromboresistant via nitric oxide release. Biomaterials 2000, 21, 9-21.

Myler, et al. Ultra-thin-polysiloxane-film-composite membranes for the optimisation of amperometric oxidase enzyme electrodes. Biosens Bioelectron 2002, 17, 35-43.

Nam, et al. A novel fabrication method of macroporous biodegradable polymer scaffolds using gas foaming salt as a porogen additive. J Biomed Mater Res 2000, 53, 1-7.

Palmisano, et al. Simultaneous monitoring of glucose and lactate by an interference and cross-talk free dual electrode amperometric biosensor based on electropolymerized thin films. Biosens Bioelectron 2000, 15, 531-539.

Pitzer, et al. Detection of hypoglycemia with the GlucoWatch biographer. Diabetes Care 2001, 24, 881-5.

Poitout, et al. A glucose monitoring system for on line estimation in man of blood glucose concentration using a miniaturized glucose sensor implanted in the subcutaneous tissue and a wearable control unit. Diabetologia 1993, 36, 658-663.

Postlethwaite, et al. Interdigitated Array Electrode as an Alternative to the Rotated Ring-Disk Electrode for Determination of the Reaction Products of Dioxygen Reduction. Analytical Chemistry 1996, 68, 2951-2958.

Ratner, B.D. Reducing capsular thickness and enhancing angiogenesis around implant drug release systems. J Control Release 2002, 78, 211-218.

Reach, Gerard, "Letters to the Editor Re: Diabetes Technology & Therapeutics, 2000;2:49-56," vol. 3, No. 1, p. 129-130, 2001.

Rhodes et al., Prediction of pocket-portable and implantable glucose enzyme electrode performance from combined species permeability and digital simulation analysis. Analytical Chemistry 1994, 66, 1520-1529.

Sansen, et al. A smart sensor for the voltammetric measurement of oxygen or glucose concentrations. Sensors and Actuators 1990, 1, 298-302.

Sansen, et al. "Glucose sensor with telemetry system." Ko, W.H. (Ed). Implantable Sensors for Closed Loop Prosthetic Systems, Ch. 12, 167-175, Futura Publishing Co. (1985).

Schmidt, et al. Glucose concentration in subcutaneous extracellular space. Diabetes Care 1993, 16, 695-700.

Schoemaker, et al. The SCGM1 System: Subcutaneous Continuous Glucose Monitoring Based on Microdialysis Technique. Diabetes Technol Ther 2003, 5, 599-608.

Shults, et al. A telemetry-instrumentation system for monitoring multiple subcutaneously implanted glucose sensors. IEEE Transactions on Biomedical Engineering 1994, 41, 937-942.

Sieminski, et al. Biomaterial-microvasculature interactions. Biomaterials 2000, 21, 2233-2241.

Skyler, J. S. The economic burden of diabetes and the benefits of improved glycemic control: the potential role of a continuous glucose monitoring system. Diabetes Technol Ther 2000, 2 Suppl 1, S7-12.

Steil, et al. Determination of plasma glucose during rapid glucose excursions with a subcutaneous glucose sensor. Diabetes Technol Ther 2003, 5, 27-31.

Tanenberg, et al. Continuous glucose monitoring system: a new approach to the diagnosis of diabetic gastroparesis. Diabetes Technol Ther 2000, 2 Suppl 1, S73-80.

Tang, et al. Fibrin(ogen) mediates acute inflammatory responses to biomaterials. J Exp Med 1993, 178, 2147-2156.

Tang, et al. Inflammatory responses to biomaterials. Am J Clin Pathol 1995, 103, 466-471.

Tang, et al. Mast cells mediate acute inflammatory responses to implanted biomaterials. Proc Natl Acad Sci U S A 1998, 95, 8841-8846.

Tang, et al. Molecular determinants of acute inflammatory responses to biomaterials. J Clin Invest 1996, 97, 1329-1334.

Thome-Duret, et. al. Modification of the sensitivity of glucose sensor implanted into subcutaneous tissue. Diabetes Metab 1996, 22, 174-178.

Tibell, et al. Survival of macroencapsulated allogeneic parathyroid tissue one year after transplantation in nonimmunosuppressed humans. Cell Transplant 2001, 10, 591-9.

Tierney, et al. The GlucoWatch biographer: a frequent automatic and noninvasive glucose monitor. Ann Med 2000, 32, 632-641.

Updike et al. Enzymatic glucose sensors: improved long-term performance in vitro and in vivo. ASAIO Journal 1994, 40, 157-163.

Updike et al. "Principles of long-term fully implanted sensors with emphasis on radiotelemetric monitoring of blood glucose from inside a subcutaneous foreign body capsule (FBC)." Fraser, D.M. (Ed.). *Biosensors in the body: continuous in vivo monitoring*, Chap. 4, pp. 117-137, John Wiley & Sons Ltd., (1997).

Updike, et al. A subcutaneous glucose sensor with improved longevity, dynamic range, and stability of calibration. Diabetes Care 2000, 23, 208-214.

Updike, et al. The enzyme electrode. Nature 1967, 214, 986-988.

Wagner, et al. A. Continuous amperometric monitoring of glucose in a brittle diabetic chimpanzee with a miniature subcutaneous electrode. Proc Natl Acad Sci U S A 1998, 95, 6379-6382.

Ward et al. A new amperometric glucose microsensor: in vitro and short-term in vivo evaluation. Biosensors & Bioelectronics 2002, 17, 181-189.

Ward, et al., Rise in background current over time in a subcutaneous glucose sensor in the rabbit: relevance to calibration and accuracy. Biosensors & Bioelectronics 2000, 15, 53-61.

Wilkins, E.; Atanasov, P.; Muggenburg, B. A., "Integrated implantable device for long-term glucose monitoring," Biosens Bioelectron 1995, 10, 485-494.

Wilson, et al. Enzyme-based biosensors for in vivo measurements. Chem Rev 2000, 100:2693-2704.

Wu, et al. In situ electrochemical oxygen generation with an immunoisolation device. Ann N Y Acad Sci 1999, 875, 105-125.

Yang, et al. Development of needle-type glucose sensor with high selectivity. Science and Actuators B 1998, 46, 249-256.

U.S. Appl. No. 09/447,227, filed Nov. 22, 1999.
U.S. Appl. No. 10/632,537, filed Aug. 1, 2003.
U.S. Appl. No. 10/633,329, filed Aug. 1, 2003.
U.S. Appl. No. 10/633,367 filed Aug. 1, 2003.
U.S. Appl. No. 10/633,404, filed Aug. 1, 2003.
U.S. Appl. No. 10/646,333, filed Aug. 22, 2003.
U.S. Appl. No. 10/648,849, filed Aug. 22, 2003.
U.S. Appl. No. 10/695,636, filed Oct. 28, 2003.
U.S. Appl. No. 10/789,359, filed Feb. 26, 2004.
U.S. Appl. No. 10/838,658, filed May 3, 2004.
U.S. Appl. No. 10/838,909, filed May 3, 2004.
U.S. Appl. No. 10/838,912, filed May 3, 2004.
U.S. Appl. No. 10/842,716, filed May 10, 2004.
U.S. Appl. No. 10/846,150, filed May 14, 2004.
U.S. Appl. No. 10/885,476, filed Jul. 6, 2004.
U.S. Appl. No. 10/896,637, filed Jul. 21, 2004.
U.S. Appl. No. 10/896,772, filed Jul. 21, 2004.
U.S. Appl. No. 10/896,639, filed Jul. 21, 2004.
U.S. Appl. No. 10/897,377, filed Jul. 21, 2004.
U.S. Appl. No. 10/896,312, filed Jul. 21, 2004.

Abel, P. U.; von Woedtke, T. Biosensors for in vivo glucose measurement: can we cross the experimental stage. Biosens Bioelectron 2002, 17, 1059-1070.

Atanasov, P.; Yang, S.; Salehi, C.; Ghindilis, A. L.; Wilkins, E.; Schade, D. Implantation of a refillable glucose monitoring-telemetry device. Biosens Bioelectron 1997, 12, 669-680.

Bowman, L.; Meindl, J. D. The packaging of implantable integrated sensors. IEEE Trans Biomed Eng 1986, 33, 248-255.

Cai, Q.; Zeng, K.; Ruan, C.; Desai, T. A.; Grimes, C. A. A wireless, remote query glucose biosensor based on a pH-sensitive polymer. Anal Chem 2004, 76, 4038-4043.

Cox, D. J.; Clarke, W. L.; Gonder-Frederick, L.; Pohl, S.; Hoover, C.; Snyder, A.; Zimbelman, L.; Carter, W. R.; Bobbitt, S.; Pennebaker, J. Accuracy of perceiving blood glucose in IDDM. Diabetes Care 1985, 8, 529-536.

El-Sa'ad, L.; Yates, D. Moisture Absorption by Epoxy Resins: the Reverse Thermal Effect. Journal of Materials Science 1990, 25, 3577-3582.

Feldman, B.; Brazg, R.; Schwartz, S.; Weinstein, R. A continuous glucose sensor based on wired enzyme technology—results from a 3-day trial in patients with type 1 diabetes. Diabetes Technol Ther 2003, 5, 769-779.

Garg, S.; Schwartz, S.; Edelman, S. Improved Glucose Excursions Using an Implantable Real-Time Continuous Glucose Sensor in Adults with Type 1 Diabetes. Diabetes Care 2004, 27, 734-738.

Gilligan, B. C.; Shults, M.; Rhodes, R. K.; Jacobs, P. G.; Brauker, J. H.; Pintar, T. J.; Updike, S. J. Feasibility of continuous long-term glucose monitoring from a subcutaneous glucose sensor in humans. Diabetes Technol Ther 2004, 6, 378-386.

Heller, A. Implanted electrochemical glucose sensors for the management of diabetes. Annu Rev Biomed Eng 1999, 1, 153-175.

Heller, A. Plugging metal connectors into enzymes. Nat Biotechnol 2003, 21, 631-2.

Hrapovic, S.; Luong, J. H. Picoamperometric detection of glucose at ultrasmall platinum-based biosensors: preparation and characterization. Anal Chem 2003, 75, 3308-3315.

Hunter, I., Jones, L., Kanigan, T., Brenan, C., Sanbol, L. Sosnowski, L. Minimally Invasive Glucose Sensor and Insulin Delivery System. MIT Home Automation and Healthcare Consortium 2000.

Jeutter, D. C. A transcutaneous implanted battery recharging and biotelemeter power switching system. IEEE Trans Biomed Eng 1982, 29, 314-321.

Kang, S. K.; Jeong, R. A.; Park, S.; Chung, T. D.; Park, S.; Kim, H. C. In vitro and short-term in vivo characteristics of a Kel-F thin film modified glucose sensor. Anal Sci 2003, 19, 1481-1486.

Kraver, K.; Guthaus, M. R.; Strong, T.; Bird, P.; Cha, G.; Hoeld, W.; Brown, R. A mixed-signal sensor interface microinstrument. Sensors and Actuators A: Physical 2001, 91, 266-277.

March, W. F. Dealing with the delay. Diabetes Technol Ther 2002, 4, 49-50.

Mastrototaro, J. J. The MiniMed continuous glucose monitoring system. Diabetes Technol Ther 2000, 2 Suppl 1, S13-8.

McCartney, L. J.; Pickup, J. C.; Rolinski, O. J.; Birch, D. J. Near-infrared fluorescence lifetime assay for serum glucose based on allophycocyanin-labeled concanavalin A. Anal Biochem 2001, 292, 216-221.

McGrath, M. J.; Iwuoha, E. I.; Diamond, D.; Smyth, M. R. The use of differential measurements with a glucose biosensor for interference compensation during glucose determinations by flow injection analysis. Biosens Bioelectron 1995, 10, 937-943.

Memoli, A.; Annesini, M. C.; Mascini, M.; Papale, S.; Petralito, S. A comparison between different immobilised glucoseoxidase-based electrodes. J Pharm Biomed Anal 2002, 29, 1045-1052.

Moatti-Sirat, D.; Capron, F.; Poitout, V.; Reach, G.; Bindra, D. S.; Zhang, Y.; Wilson, G. S.; Thevenot, D. R. Towards continuous glucose monitoring: in vivo evaluation of a miniaturized glucose sensor implanted for several days in rat subcutaneous tissue. Diabetologia 1992, 35, 224-230.

Ohara, T. J.; Rajagopalan, R.; Heller, A. "Wired", enzyme electrodes for amperometric determination of glucose or lactate in the presence of interfering substances. Anal Chem 1994, 66, 2451-2457.

Okuda, J.; Miwa, I. Mutarotase effect on micro determinations of D-glucose and its anomers with -D-glucose oxidase. Anal Biochem 1971, 43, 312-315.

Patel, H.; Li, X.; Karan, H. I. Amperometric glucose sensors based on ferrocene containing polymeric electron transfer systems-a preliminary report. Biosens Bioelectron 2003, 18, 1073-6.

Pichert, J. W.; Campbell, K.; Cox, D. J.; D'Lugin, J. J.; Moffat, J. W.; Polonsky, W. H.; CN, -. . P. o. G. D. P. S. G. Issues for the coming age of continuous glucose monitoring. Diabetes Educ 2000, 26, 969-980.

Quinn, C. A.; Connor, R. E.; Heller, A. Biocompatible, glucose-permeable hydrogel for in situ coating of implantable biosensors. Biomaterials 1997, 18, 1665-1670.

Reach, G.; Abel, P.; Fischer, U. A Method for Evaluating in vivo the Functional Characteristics of Glucose Sensors. Biosensors 1986, 2, 211-220.

Schuler, R.; Wittkampf, M.; Chemnitius, G. C. Modified gas-permeable silicone rubber membranes for covalent immobilisation of enzymes and their use in biosensor development. Analyst 1999, 124, 1181-1184.

Selam, J. L. Management of diabetes with glucose sensors and implantable insulin pumps. From the dream of the 60s to the realities of the 90s. ASAIO J 1997, 43, 137-142.

Service, R. F. Can sensors make a home in the body? Science 2002, 297, 962-3.

Shichiri, M.; Kawamori, R.; Yamasaki, Y.; Hakul, N.; Abe, H. Wearable artificial endocrine pancrease with needle-type glucose sensor. Lancet 1982, 2, 1129-1131.

Shichiri, M.; Kawamori, R.; Yamasaki, Y.; Hakul, N.; Asakawa, N.; Abe, H. Needle-type Glucose Sensor for Wearable Artificial Endocrine Pancreas. Book Implantable Sensors 1985, 197-210.

Sriyudthsak, M.; Cholapranee, T.; Sawadsaringkarn, M.; Yupongchaey, N.; Jaiwang, P. Enzyme-epoxy membrane based glucose analyzing system and medical applications. Biosens Bioelectron 1996, 11, 735-742.

Stemberg, R.; Barrau, M. B.; Gangiotti, L.; Thevenot, D. R.; Bindra, D. S.; Wilson, G. S.; Velho, G.; Froguel, P.; Reach, G. Study and development of multilayer needle-type enzyme-based glucose microsensors. Biosensors 1989, 4, 27-40.

Thome-Duret, V.; Aussedat, B.; Reach, G.; Gangnerau, M. N.; Lemonnier, F.; Klein, J. C.; Zhang, Y.; Hu, Y.; Wilson, G. S. Continuous glucose monitoring in the free-moving rat. Metabolism 1998, 47, 799-803.

Tierney, M. J.; Garg, S.; Ackerman, N. R.; Germi, S. J.; Kennedy, J.; Lopatin, M.; Potts, R. O.; Tamada, J. A. Effect of acetaminophen on the accuracy of glucose measurements obtained with the GlucoWatch biographer. Diabetes Technol Ther 2000, 2, 199-207.

Trecroci, D. A Glimpse into the Future- Continuous Monitoring of Glucose with a Microfiber. Diabetes Interview 2002, 42-43.

Velho, G.; Froguel, P.; Sternberg, R.; Thevenot, D. R.; Reach, G. In vitro and in vivo stability of electrode potentials in needle-type glucose sensors. Influence of needle material. Diabetes 1989, 38, 164-171.

Wang, J.; Liu, J.; Chen, L.; Lu, F. Highly Selective Membrane-Free, Mediator-Free Glucose Biosensor. Anal. Chem. 1994, 66, 3600-3603.

Wang, X.; Pardue, H. L. Improved ruggedness for membrane-based amperometric sensors using a pulsed amperometric method. Anal Chem 1997, 69, 4482-4489.

Ward, W. K.; Wood, M. D.; Troupe, J. E. Understanding Spontaneous Output Fluctuations of an Amperometric Glucose Sensor: Effect of Inhalation Anesthesia and Use of a Nonenzyme Containing Electrode. ASAIO Journal 2000, 540-546.

Wienties, K. J. C. Development of a glucose sensor for diabetic patients. 2000.

Wilkins, E.; Atanasov, P. Glucose monitoring: state of the art and future possibilities. Med Eng Phys 1995, 18, 273-288.

Wood, W., et al., Hermetic Sealing with Epoxy. Mechanical Engineering Mar. 1990, 1-3.

PCT International Search Report for PCT International Application No. PCT/US2004/015846, mailed on May 12, 2005.

Written Opinion of the International Searching Authority for PCT International Application No. PCT/US2004/015846, mailed on May 12, 2005.

POROUS MEMBRANES FOR USE WITH IMPLANTABLE DEVICES

RELATED APPLICATION

This application claims the benefit of U.S. Provisional Application No. 60/472,673 filed May 21, 2003.

FIELD OF THE INVENTION

The preferred embodiments relate generally to biointerface membranes that can be utilized with implantable devices such as devices for the detection of analyte concentrations in a biological sample (e.g., a body), cell transplantation devices, drug delivery devices, electrical signal delivering or measuring devices, and/or combinations thereof.

BACKGROUND OF THE INVENTION

Some medical devices, including implanted analyte sensors, drug delivery devices and cell transplantation devices require close vascularization and transport of solutes across the device-tissue interface for proper function. These devices generally include a biointerface membrane, which encases the device or a portion of the device to prevent access by host inflammatory cells, immune cells, or soluble factors to sensitive regions of the device.

A disadvantage of conventional biointerface membranes is that they often stimulate a local inflammatory response, called the foreign body response (FBR), which has long been recognized as limiting the function of implanted devices that require solute transport. The FBR has been well described in the literature.

FIG. 1 is a schematic drawing that illustrates a classical FBR to a conventional synthetic membrane 10 implanted under the skin. There are three main layers of a FBR. The innermost FBR layer 12, adjacent to the device, is composed generally of macrophages and foreign body giant cells 14 (herein referred to as the barrier cell layer). These cells form a monolayer of closely opposed cells over the entire surface of a microscopically smooth, macroscopically smooth (but microscopically rough), or microporous (i.e., less than about 1 µm) membrane. Particularly, it is noted that the membrane can be adhesive or non-adhesive to cells, however its relatively smooth surface causes the downward tissue contracture 21 (discussed below) to translate directly to the cells at the device-tissue interface 26. The intermediate FBR layer 16 (herein referred to as the fibrous zone), lying distal to the first layer with respect to the device, is a wide zone (about 30–100 microns) composed primarily of fibroblasts 18, contractile fibrous tissue 19 fibrous matrixes 20. It is noted that the organization of the fibrous zone, and particularly the contractile fibrous tissue 19, contributes to the formation of the monolayer of closely opposed cells due to the contractile forces 21 around the surface of the foreign body (e.g., membrane 10). The outermost FBR layer 22 is loose connective granular tissue containing new blood vessels 24 (herein referred to as the vascular zone). Over time, this FBR tissue becomes muscular in nature and contracts around the foreign body so that the foreign body remains tightly encapsulated. Accordingly, the downward forces 21 press against the tissue-device interface 26, and without any counteracting forces, aid in the formation of a barrier cell layer 14 that blocks and/or refracts the transport of analytes 23 (e.g., glucose) across the tissue-device interface 26.

A consistent feature of the innermost layers 12, 16 is that they are devoid of blood vessels. This has led to widely supported speculation that poor transport of molecules across the device-tissue interface 26 is due to a lack of vascularization near the interface. See Scharp et al., World J. Surg., 8:221–229 (1984); and Colton and Avgoustiniatos, J. Biomech. Eng., 113:152–170 (1991). Previous efforts to overcome this problem have been aimed at increasing local vascularization at the device-tissue interface, but have achieved only limited success.

FIG. 2 is a schematic view that illustrates a conventional bilayer membrane 28 that has cell impermeable layers that are adhesive to cells. Although the conventional bilayer membrane of this example has allowed some blood vessels 24 to be brought close to the implant membrane 28, the cell impenetrable layers are porous and cells 14 are able to reach pseudopodia into the interstices (e.g., pores) of the membrane to attach to and/or flatten on the membrane, as shown in both FIGS. 1 and 2, thereby blocking transport of molecules (e.g., glucose) across the membrane-tissue interface 26.

This layer of cells 12 forms a monolayer with closely opposed cells 14 having tight cell-to-cell junctions, due to cellular attachment and/or contractile forces 21 of fibrous tissue 19, for example. When this barrier cell layer forms, it is not substantially overcome by increased local vascularization. Although local vascularization aids in sustenance of local tissue over time, the barrier cell layer 12 prevents the passage of molecules that cannot diffuse through the layer. Again, this is illustrated in FIG. 2 where blood vessels can be close to the membrane but analyte transport is significantly reduced due to the impermeable nature of the barrier cell layer. For example, when applied to an implantable glucose sensor, both glucose and its phosphorylated form do not readily transit the cell membrane. Consequently, little glucose reaches the implant membrane through the barrier cell layer.

The known art purports to increase the local vascularization in order to increase solute availability. However, it has been observed that once the monolayer of cells (barrier cell layer) is established adjacent to a membrane, increasing angiogenesis is not sufficient to increase transport of molecules such as glucose and oxygen across the device-tissue interface 26. In fact, the barrier cell layer blocks and/or refracts the analytes 23 from transport across the device-tissue interface 26. Materials or membranes employed in implantable devices are described in Brauker et al. (U.S. Pat. No. 5,741,330), Seare, Jr. (U.S. Pat. No. 5,681,572), and Picha (U.S. Pat. No. 5,564,439).

SUMMARY OF THE INVENTION

There is a need for a membrane for implantation in soft tissue that supports tissue ingrowth, interferes with and resists barrier cell layer formation, and allows the transport of analytes across the membrane.

Accordingly, in a first embodiment a biointerface membrane suitable for implantation in a soft tissue of an animal is provided, the membrane including: a first domain, wherein the first domain supports tissue ingrowth and interferes with barrier cell layer formation, wherein the first domain includes a plurality of interconnected cavities and a solid portion, and wherein a substantial number of the interconnected cavities are greater than or equal to about 90 microns in at least one dimension; and a second domain, wherein the second domain allows passage of an analyte, and wherein the second domain is resistant to cellular attachment and is impermeable to cells and cell processes.

In an aspect of the first embodiment, the first domain includes a depth of greater than one cavity in three dimensions substantially throughout an entirety of the first domain.

In an aspect of the first embodiment, the cavities and a plurality of cavity interconnections are formed in a plurality of layers having different cavity dimensions.

In an aspect of the first embodiment, a substantial number of the cavities are greater than or equal to about 160 microns in at least one dimension.

In an aspect of the first embodiment, a substantial number of the cavities are greater than or equal to about 220 microns in at least one dimension.

In an aspect of the first embodiment, a substantial number of the cavities are greater than or equal to about 285 microns in at least one dimension.

In an aspect of the first embodiment, a substantial number of the cavities are greater than or equal to about 350 microns in at least one dimension.

In an aspect of the first embodiment, a substantial number of the cavities are greater than or equal to about 370 microns in at least one dimension.

In an aspect of the first embodiment, a substantial number of the cavities are from about 90 microns to about 370 microns in at least one dimension.

In an aspect of the first embodiment, a substantial number of the cavities are from about 220 microns to about 350 microns in at least one dimension.

In an aspect of the first embodiment, a substantial number of the cavities are from about 220 microns to about 285 microns in at least one dimension.

In an aspect of the first embodiment, a substantial number of the cavities are less than or equal to about 1000 microns in a longest dimension.

In an aspect of the first embodiment, a substantial number of the cavities are less than or equal to about 500 microns in a longest dimension.

In an aspect of the first embodiment, a substantial number of shortest dimensions of the solid portion are greater than or equal to about 5 microns and wherein a substantial number of longest dimensions of the solid portion are greater than or equal to about 2000 microns.

In an aspect of the first embodiment, a substantial number of shortest dimensions of the solid portion are greater than or equal to about 10 microns and wherein a substantial number of longest dimensions of the solid portion are greater than or equal to about 1000 microns.

In an aspect of the first embodiment, a substantial number of shortest dimensions of the solid portion are greater than or equal to about 10 microns and wherein a substantial number of longest dimensions of the solid portion are greater than or equal to about 400 microns.

In an aspect of the first embodiment, the solid portion includes silicone.

In an aspect of the first embodiment, he solid portion includes polyurethane.

In an aspect of the first embodiment, the solid portion includes a block copolymer.

In an aspect of the first embodiment, the solid portion includes a material selected from the group consisting of polytetrafluoroethylene, polyethylene-co-tetrafluoroethylene, polyolefin, polyester, and polycarbonate.

In an aspect of the first embodiment, the second domain includes a biostable material.

In an aspect of the first embodiment, the biostable material includes polyurethane and a hydrophilic polymer.

In an aspect of the first embodiment, the biostable material includes polyurethane and polyvinylpyrrolidone.

In an aspect of the first embodiment, the second domain includes greater than or equal to about 5 wt. % polyurethane and greater than or equal to about 45 wt. % polyvinylpyrrolidone.

In an aspect of the first embodiment, the second domain includes greater than or equal to about 20 wt. % polyurethane and greater than or equal to about 35 wt. % polyvinylpyrrolidone.

In an aspect of the first embodiment, the second domain includes polyurethane and about 27 wt. % polyvinylpyrrolidone.

In an aspect of the first embodiment, the second domain includes a silicone copolymer.

In an aspect of the first embodiment, the analyte includes glucose.

In a second embodiment, a sensor head suitable for use in an implantable device is provided, the sensor head including: a biointerface membrane, the biointerface membrane including: a first domain, wherein the first domain supports tissue ingrowth and interferes with barrier cell layer formation, wherein the first domain includes a plurality of interconnected cavities and a solid portion, and wherein a substantial number of the cavities are greater than or equal to about 90 microns in at least one dimension; and a second domain, wherein the second domain allows passage of an analyte, and wherein the second domain is resistant to cellular attachment and is impermeable to cells and cell processes.

In an aspect of the second embodiment, the first domain includes a depth of greater than one cavity in three dimensions substantially throughout an entirety of the first domain.

In an aspect of the second embodiment, the cavities and a plurality of cavity interconnections are formed in a plurality of layers having different cavity dimensions.

In an aspect of the second embodiment, a substantial number of the cavities are greater than or equal to about 160 microns in at least one dimension.

In an aspect of the second embodiment, a substantial number of the cavities are greater than or equal to about 220 microns in at least one dimension.

In an aspect of the second embodiment, a substantial number of the cavities are greater than or equal to about 285 microns in at least one dimension.

In an aspect of the second embodiment, a substantial number of the cavities are greater than or equal to about 350 microns in at least one dimension.

In an aspect of the second embodiment, a substantial number of the cavities are greater than or equal to about 370 microns in at least one dimension.

In an aspect of the second embodiment, a substantial number of the cavities are from about 90 microns to about 370 microns in at least one dimension.

In an aspect of the second embodiment, a substantial number of the cavities are from about 220 microns to about 350 microns in at least one dimension.

In an aspect of the second embodiment, a substantial number of the cavities are from about 220 microns to about 285 microns in at least one dimension.

In an aspect of the second embodiment, a substantial number of the cavities are less than or equal to about 1000 microns in a longest dimension.

In an aspect of the second embodiment, a substantial number of the cavities are less than or equal to about 500 microns in a longest dimension.

In an aspect of the second embodiment, a substantial number of shortest dimensions of the solid portion are greater than or equal to about 5 microns and wherein a substantial number of longest dimensions of the solid portion are greater than or equal to about 2000 microns.

In an aspect of the second embodiment, a substantial number of shortest dimensions of the solid portion are greater than or equal to about 10 microns and wherein a substantial number of longest dimensions of the solid portion are greater than or equal to about 1000 microns.

In an aspect of the second embodiment, a substantial number of shortest dimensions of the solid portion are greater than or equal to about 10 microns and wherein a substantial number of longest dimensions of the solid portion are greater than or equal to about 400 microns.

In an aspect of the second embodiment, the solid portion includes silicone.

The sensor head according to claim 29, wherein the solid portion includes polyurethane.

In an aspect of the second embodiment, the solid portion includes a block copolymer.

In an aspect of the second embodiment, the solid portion includes a material selected from the group consisting of polytetrafluoroethylene, polyethylene-co-tetrafluoroethylene, polyolefin, polyester, and polycarbonate.

In an aspect of the second embodiment, the second domain includes a biostable material.

In an aspect of the second embodiment, the biostable material includes polyurethane and a hydrophilic polymer.

In an aspect of the second embodiment, the biostable material includes polyurethane and polyvinylpyrrolidone.

In an aspect of the second embodiment, the second domain includes greater than or equal to about 5 wt. % polyurethane and greater than or equal to about 45 wt. % polyvinylpyrrolidone.

In an aspect of the second embodiment, the second domain includes greater than or equal to about 20 wt. % polyurethane and greater than or equal to about 35 wt. % polyvinylpyrrolidone.

In an aspect of the second embodiment, the second domain includes polyurethane and about 27 wt. % polyvinylpyrrolidone.

In an aspect of the second embodiment, the second domain includes a silicone copolymer.

In an aspect of the second embodiment, the analyte includes glucose.

In a third embodiment, an analyte measuring device for measuring a concentration of an analyte in a body is provided, the device including: a biointerface membrane, the biointerface membrane including: a first domain, wherein the first domain supports tissue ingrowth and interferes with barrier cell layer formation, wherein the first domain includes a plurality of interconnected cavities and a solid portion, and wherein a substantial number of the cavities are greater than or equal to about 90 microns in at least one dimension; and a second domain, wherein the second domain allows passage of an analyte, and wherein the second domain is resistant to cellular attachment and is impermeable to cells and cell processes.

In an aspect of the third embodiment, the first domain includes a depth of greater than one cavity in three dimensions substantially throughout an entirety of the first domain.

In an aspect of the third embodiment, the cavities and a plurality of cavity interconnections are formed in a plurality of layers having different cavity dimensions.

In an aspect of the third embodiment, a substantial number of the cavities are greater than or equal to about 160 microns in at least one dimension.

In an aspect of the third embodiment, a substantial number of the cavities are greater than or equal to about 220 microns in at least one dimension.

In an aspect of the third embodiment, a substantial number of the cavities are greater than or equal to about 285 microns in at least one dimension.

In an aspect of the third embodiment, a substantial number of the cavities are greater than or equal to about 350 microns in at least one dimension.

In an aspect of the third embodiment, a substantial number of the cavities are greater than or equal to about 370 microns in at least one dimension.

In an aspect of the third embodiment, a substantial number of the cavities are from about 90 microns to about 370 microns in at least one dimension.

In an aspect of the third embodiment, a substantial number of the cavities are from about 220 microns to about 350 microns in at least one dimension.

In an aspect of the third embodiment, a substantial number of the cavities are from about 220 microns to about 285 microns in at least one dimension.

In an aspect of the third embodiment, a substantial number of the cavities are less than or equal to about 1000 microns in a longest dimension.

In an aspect of the third embodiment, a substantial number of the cavities are less than or equal to about 500 microns in a longest dimension.

In an aspect of the third embodiment, a substantial number of shortest dimensions of the solid portion are greater than or equal to about 5 microns and wherein a substantial number of longest dimensions of the solid portion are greater than or equal to about 2000 microns.

In an aspect of the third embodiment, a substantial number of shortest dimensions of the solid portion are greater than or equal to about 10 microns and wherein a substantial number of longest dimensions of the solid portion are greater than or equal to about 1000 microns.

In an aspect of the third embodiment, a substantial number of shortest dimensions of the solid portion are greater than or equal to about 10 microns and wherein a substantial number of longest dimensions of the solid portion are greater than or equal to about 400 microns.

In an aspect of the third embodiment, the solid portion includes silicone.

In an aspect of the third embodiment, the solid portion includes polyurethane.

In an aspect of the third embodiment, the solid portion includes a block copolymer.

In an aspect of the third embodiment, the solid portion includes a material selected from the group consisting of polytetrafluoroethylene, polyethylene-co-tetrafluoroethylene, polyolefin, polyester, and polycarbonate.

In an aspect of the third embodiment, the second domain includes a biostable material.

In an aspect of the third embodiment, the biostable material includes polyurethane and a hydrophilic polymer.

In an aspect of the third embodiment, the biostable material includes polyurethane and polyvinylpyrrolidone.

In an aspect of the third embodiment, the second domeain includes greater than or equal to about 5 wt. % polyurethane and greater than or equal to about 45 wt. % polyvinylpyrrolidone.

In an aspect of the third embodiment, the second domain includes greater than or equal to about 20 wt. % polyurethane and greater than or equal to about 35 wt. % polyvinylpyrrolidone.

In an aspect of the third embodiment, the second domain includes polyurethane and about 27 wt. % polyvinylpyrrolidone.

In an aspect of the third embodiment, the second domain includes a silicone copolymer.

In an aspect of the third embodiment, the device further includes a housing and at least one sensor head, wherein the housing includes electronic circuitry; and wherein the sensor head is operably connected to the electronic circuitry, wherein the biointerface membrane covers the sensor head.

In an aspect of the third embodiment, the analyte measuring device includes a glucose monitoring device.

In a fourth embodiment, an implantable glucose sensor suitable for measuring glucose in a biological fluid is provided, the sensor including: a housing and at least one sensor head, wherein the housing includes electronic circuitry and wherein the sensor head is operably connected to the electronic circuitry, the sensor head including a biointerface membrane, the biointerface membrane including: a first domain, wherein the first domain supports tissue ingrowth and interferes with barrier cell layer formation, wherein the first domain includes a plurality of interconnected cavities and a solid portion, and wherein a substantial number of the cavities are greater than or equal to about 90 microns in at least one dimension; and a second domain, wherein the second domain allows passage of glucose, and wherein the second domain is resistant to cellular attachment and is impermeable to cells and cell processes.

In an aspect of the fourth embodiment, the first domain includes a depth of greater than one cavity in three dimensions substantially throughout an entirety of the first domain.

In an aspect of the fourth embodiment, the cavities and a plurality of cavity interconnections are formed in a plurality of layers having different cavity dimensions.

In an aspect of the fourth embodiment, a substantial number of the cavities are greater than or equal to about 160 microns in at least one dimension.

In an aspect of the fourth embodiment, a substantial number of the cavities are greater than or equal to about 220 microns in at least one dimension.

In an aspect of the fourth embodiment, a substantial number of the cavities are greater than or equal to about 285 microns in at least one dimension.

In an aspect of the fourth embodiment, a substantial number of the cavities are greater than or equal to about 350 microns in at least one dimension.

In an aspect of the fourth embodiment, a substantial number of the cavities are greater than or equal to about 370 microns in at least one dimension.

In an aspect of the fourth embodiment, a substantial number of the cavities are from about 90 microns to about 370 microns in at least one dimension.

In an aspect of the fourth embodiment, a substantial number of the cavities are from about 220 microns to about 350 microns in at least one dimension.

In an aspect of the fourth embodiment, a substantial number of the cavities are from about 220 microns to about 285 microns in at least one dimension.

In an aspect of the fourth embodiment, a substantial number of the cavities are less than or equal to about 1000 microns in a longest dimension.

In an aspect of the fourth embodiment, a substantial number of the cavities are less than or equal to about 500 microns in a longest dimension.

In an aspect of the fourth embodiment, a substantial number of shortest dimensions of the solid portion are greater than or equal to 5 microns and wherein a substantial number of longest dimensions of the solid portion are greater than or equal to about 2000 microns.

In an aspect of the fourth embodiment, a substantial number of shortest dimensions of the solid portion are greater than or equal to about 10 microns and wherein a substantial number of longest dimensions of the solid portion are greater than or equal to about 1000 microns.

In an aspect of the fourth embodiment, a substantial number of shortest dimensions of the solid portion are greater than or equal to about 10 microns and wherein a substantial number of longest dimensions of the solid portion are greater than or equal to about 400 microns.

In an aspect of the fourth embodiment, the solid portion includes silicone.

In an aspect of the fourth embodiment, the solid portion includes polyurethane.

In an aspect of the fourth embodiment, the solid portion includes a block copolymer.

In an aspect of the fourth embodiment, the solid portion includes a material selected from the group consisting of polytetrafluoroethylene, polyethylene-co-tetrafluoroethylene, polyolefin, polyester, and polycarbonate.

In an aspect of the fourth embodiment, the second domain includes a biostable material.

In an aspect of the fourth embodiment, the biostable material includes polyurethane and a hydrophilic polymer.

In an aspect of the fourth embodiment, the biostable material includes polyurethane and polyvinylpyrrolidone.

In an aspect of the fourth embodiment, the second domain includes greater than or equal to about 5 wt. % polyurethane and greater than or equal to about 45 wt. % polyvinylpyrrolidone.

In an aspect of the fourth embodiment, the second domain includes greater than or equal to about 20 wt. % polyurethane and greater than or equal to about 35 wt. % polyvinylpyrrolidone.

In an aspect of the fourth embodiment, the second domain includes polyurethane and about 27 wt. % polyvinylpyrrolidone.

In an aspect of the fourth embodiment, the second domain includes a silicone copolymer.

In a fifth embodiment, a biointerface membrane suitable for implantation in a soft tissue is provided, the membrane including: a first domain including a plurality of interconnected cavities and a solid portion, wherein the first domain has a depth of greater than one cavity in three dimensions substantially throughout an entirety of the first domain, and wherein the plurality of interconnected cavities and the solid portion of the first domain are dimensioned and arranged to redirect fibrous tissue contracture in vivo, thereby interfering with barrier cell layer formation within or around the first domain; and a second domain, the second domain allowing passage of an analyte, wherein the second domain is resistant to cellular attachment and is impermeable to cells and cell processes.

In an aspect of the fifth embodiment, a substantial number of the cavities are greater than or equal to about 90 microns in at least one dimension.

In an aspect of the fifth embodiment, the cavities and a plurality of cavity interconnections are formed in a plurality of layers having different cavity dimensions.

In an aspect of the fifth embodiment, a substantial number of the cavities are greater than or equal to about 160 microns in at least one dimension.

In an aspect of the fifth embodiment, a substantial number of the cavities are greater than or equal to about 220 microns in at least one dimension.

In an aspect of the fifth embodiment, a substantial number of the cavities are greater than or equal to about 285 microns in at least one dimension.

In an aspect of the fifth embodiment, a substantial number of the cavities are greater than or equal to about 350 microns in at least one dimension.

In an aspect of the fifth embodiment, a substantial number of the cavities are greater than or equal to about 370 microns in at least one dimension.

In an aspect of the fifth embodiment, a substantial number of the cavities are from about 90 microns to about 370 microns in at least one dimension.

In an aspect of the fifth embodiment, a substantial number of the cavities are from about 220 microns to about 350 microns in at least one dimension.

In an aspect of the fifth embodiment, a substantial number of the cavities are from about 220 microns to about 285 microns in at least one dimension.

In an aspect of the fifth embodiment, a substantial number of the cavities are less than or equal to about 1000 microns in a longest dimension.

In an aspect of the fifth embodiment, a substantial number of the cavities are less than or equal to about 500 microns in a longest dimension.

In an aspect of the fifth embodiment, a substantial number of shortest dimensions of the solid portion are greater than or equal to about 5 microns and wherein a substantial number of longest dimensions of the solid portion are greater than or equal to about 2000 microns.

In an aspect of the fifth embodiment, a substantial number of shortest dimensions of the solid portion are greater than or equal to about 10 microns and wherein a substantial number of longest dimensions of the solid portion are greater than or equal to about 1000 microns.

In an aspect of the fifth embodiment, a substantial number of shortest dimensions of the solid portion are greater than or equal to about 10 microns and wherein a substantial number of longest dimensions of the solid portion are greater than or equal to about 400 microns.

In an aspect of the fifth embodiment, the solid portion includes silicone.

In an aspect of the fifth embodiment, the solid portion includes polyurethane.

In an aspect of the fifth embodiment, the solid portion includes a block copolymer.

In an aspect of the fifth embodiment, the solid portion includes a material selected from the group consisting of polytetrafluoroethylene, polyethylene-co-tetrafluoroethylene, polyolefin, polyester, and polycarbonate.

In an aspect of the fifth embodiment, the second domain includes a biostable material.

In an aspect of the fifth embodiment, the biostable material includes polyurethane and a hydrophilic polymer.

In an aspect of the fifth embodiment, the biostable material includes polyurethane and polyvinylpyrrolidone.

In an aspect of the fifth embodiment, the second domain includes greater than or equal to about 5 wt. % polyurethane and greater than or equal to about 45 wt. % polyvinylpyrrolidone.

In an aspect of the fifth embodiment, the second domain includes greater than or equal to about 20 wt. % polyurethane and greater than or equal to about 35 wt. % polyvinylpyrrolidone.

In an aspect of the fifth embodiment, the second domain includes polyurethane and about 27 wt. % polyvinylpyrrolidone.

In an aspect of the fifth embodiment, the second domain includes a silicone copolymer.

In an aspect of the fifth embodiment, the analyte includes glucose.

In a sixth embodiment, a membrane suitable for implantation in a soft tissue is provided, the membrane including: a first domain, the first domain including a plurality of interconnected cavities and a solid portion; and a second domain, the second domain allowing the passage of an analyte, wherein the second domain is resistant to cellular attachment and is impermeable to cells and cell processes, wherein the plurality of interconnected cavities and solid portion of the first domain are dimensioned and arranged to create a contractile force directed against the solid portion that counteracts a generally uniform downward fibrous tissue contracture caused by a foreign body response in vivo, thereby interfering with barrier cell layer formation proximal to the second domain.

In an aspect of the sixth embodiment, a substantial number of the cavities are greater than or equal to about 90 microns in at least one dimension.

In an aspect of the sixth embodiment, the cavities and a plurality of cavity interconnections are formed in a plurality of layers having different cavity dimensions.

In an aspect of the sixth embodiment, a substantial number of the cavities are greater than or equal to about 160 microns in at least one dimension.

In an aspect of the sixth embodiment, a substantial number of the cavities are greater than or equal to about 220 microns in at least one dimension.

In an aspect of the sixth embodiment, a substantial number of the cavities are greater than or equal to about 285 microns in at least one dimension.

In an aspect of the sixth embodiment, a substantial number of the cavities are greater than or equal to about 350 microns in at least one dimension.

In an aspect of the sixth embodiment, a substantial number of the cavities are greater than or equal to about 370 microns in at least one dimension.

In an aspect of the sixth embodiment, a substantial number of the cavities are from about 90 microns to about 370 microns in at least one dimension.

In an aspect of the sixth embodiment, a substantial number of the cavities are from about 220 microns to about 350 microns in at least one dimension.

In an aspect of the sixth embodiment, a substantial number of the cavities are from about 220 microns to about 285 microns in at least one dimension.

In an aspect of the sixth embodiment, a substantial number of the cavities are less than or equal to about 1000 microns in a longest dimension.

In an aspect of the sixth embodiment, a substantial number of the cavities are less than or equal to about 500 microns in a longest dimension.

In an aspect of the sixth embodiment, a substantial number of shortest dimensions of the solid portion are greater than or equal to about 5 microns and wherein a substantial number of longest dimensions of the solid portion are greater than or equal to about 2000 microns.

In an aspect of the sixth embodiment, a substantial number of shortest dimensions of the solid portion are greater than or equal to about 10 microns and wherein a substantial number of longest dimensions of the solid portion are greater than or equal to about 1000 microns.

In an aspect of the sixth embodiment, a substantial number of shortest dimensions of the solid portion are greater than or equal to about 10 microns and wherein a substantial number of longest dimensions of the solid portion are greater than or equal to about 400 microns.

In an aspect of the sixth embodiment, the solid portion includes silicone.

In an aspect of the sixth embodiment, the solid portion includes polyurethane.

In an aspect of the sixth embodiment, the solid portion includes a block copolymer.

In an aspect of the sixth embodiment, the solid portion includes a material selected from the group consisting of polytetrafluoroethylene, polyethylene-co-tetrafluoroethylene, polyolefin, polyester, and polycarbonate.

In an aspect of the sixth embodiment, the second domain includes a biostable material.

In an aspect of the sixth embodiment, the biostable material includes polyurethane and a hydrophilic polymer.

In an aspect of the sixth embodiment, the biostable material includes polyurethane and polyvinylpyrrolidone.

In an aspect of the sixth embodiment, the second domain includes greater than or equal to about 5 wt. % polyurethane and greater than or equal to about 45 wt. % polyvinylpyrrolidone.

In an aspect of the sixth embodiment, the second domain includes greater than or equal to about 20 wt. % polyurethane and greater than or equal to about 35 wt. % polyvinylpyrrolidone.

In an aspect of the sixth embodiment, the second domain includes polyurethane and about 27 wt. % polyvinylpyrrolidone.

In an aspect of the sixth embodiment, the second domain includes a silicone copolymer.

In an aspect of the sixth embodiment, the analyte includes glucose.

In a seventh embodiment, a method of monitoring an analyte level is provided, the method including the steps of: providing an implantable device configured to monitor an analyte level, the implantable device including a biointerface membrane, wherein the biointerface membrane includes: a first domain, wherein the first domain includes a plurality of interconnected cavities and a solid portion, wherein the plurality of interconnected cavities and solid portion of the first domain are dimensioned and arranged to create a contractile force directed against the solid portion that counteracts a generally uniform downward fibrous tissue contracture caused by a foreign body response in vivo, thereby interfering with barrier cell layer formation within or around the first domain; and a second domain, the second domain allowing the passage of an analyte, wherein the second domain is resistant to cellular attachment and is impermeable to cells and cell processes; implanting the implantable device in the host; and monitoring an analyte level.

In an aspect of the seventh embodiment, the step of implanting includes subcutaneously implanting.

In an aspect of the seventh embodiment, the step of implanting includes intramuscular implanting.

In an aspect of the seventh embodiment, the step of implanting includes intraperotoneal implanting.

In an aspect of the seventh embodiment, the step of implanting includes intrafascial implanting.

In an aspect of the seventh embodiment, the step of implanting includes implanting in an axillary region.

In an aspect of the seventh embodiment, the step of implanting includes implanting in soft tissue.

In an aspect of the seventh embodiment, the solid portion includes silicone.

The method according to claim 169, wherein the solid portion includes polyurethane.

In an aspect of the seventh embodiment, the solid portion includes a block copolymer.

In an aspect of the seventh embodiment, the solid portion includes a material selected from the group consisting of polytetrafluoroethylene, polyethylene-co-tetrafluoroethylene, polyolefin, polyester, and polycarbonate.

In an aspect of the seventh embodiment, the second domain includes a biostable material.

In an aspect of the seventh embodiment, the biostable material includes polyurethane and a hydrophilic polymer.

In an aspect of the seventh embodiment, the biostable material includes polyurethane and polyvinylpyrrolidone.

In an aspect of the seventh embodiment, the second domain includes greater than or equal to about 5 wt. % polyurethane and greater than or equal to about 45 wt. % polyvinylpyrrolidone.

In an aspect of the seventh embodiment, the second domain includes greater than or equal to about 20 wt. % polyurethane and greater than or equal to about 35 wt. % polyvinylpyrrolidone.

In an aspect of the seventh embodiment, the second domain includes polyurethane and about 27 wt. % polyvinylpyrrolidone.

In an aspect of the seventh embodiment, the second domain includes a silicone copolymer.

In an aspect of the seventh embodiment, the analyte includes glucose.

In an eighth embodiment, a method of monitoring an analyte level is provided, the method including the steps of: providing an implantable device, the implantable device including a housing and at least one sensor head, the housing including electronic circuitry, wherein the sensor head is operably connected to the electronic circuitry, the sensor head including a biointerface membrane, the biointerface membrane including: a first domain, wherein the first domain supports tissue ingrowth and interferes with barrier cell layer formation, wherein the first domain includes a plurality of interconnected cavities and a solid portion, and wherein a substantial number of the cavities are greater than or equal to about 90 microns in at least one dimension; and a second domain, the second domain allowing passage of an analyte, wherein the second domain is resistant to cellular attachment and is impermeable to cells and cell processes; implanting the implantable device in a host; and monitoring an analyte level.

In an aspect of the eighth embodiment, the step of implanting includes subcutaneously implanting.

In an aspect of the eighth embodiment, the first domain includes a depth of greater than one cavity in three dimensions substantially throughout an entirety of the first domain.

In an aspect of the eighth embodiment, the cavities and a plurality of cavity interconnections are formed in a plurality of layers having different cavity dimensions.

In an aspect of the eighth embodiment, a substantial number of the cavities are greater than or equal to about 160 microns in at least one dimension.

In an aspect of the eighth embodiment, a substantial number of the cavities are greater than or equal to about 220 microns in at least one dimension.

In an aspect of the eighth embodiment, a substantial number of the cavities are greater than or equal to about 285 microns in at least one dimension.

In an aspect of the eighth embodiment, a substantial number of the cavities are greater than or equal to about 350 microns in at least one dimension.

In an aspect of the eighth embodiment, a substantial number of the cavities are greater than or equal to about 370 microns in at least one dimension.

In an aspect of the eighth embodiment, a substantial number of the cavities are from about 90 microns to about 370 microns in at least one dimension.

In an aspect of the eighth embodiment, a substantial number of the cavities are from about 220 microns to about 350 microns in at least one dimension.

In an aspect of the eighth embodiment, a substantial number of the cavities are from about 220 microns to about 285 microns in at least one dimension.

In an aspect of the eighth embodiment, a substantial number of the cavities are less than or equal to about 1000 microns in a longest dimension.

In an aspect of the eighth embodiment, a substantial number of the cavities are less than or equal to about 500 microns in a longest dimension.

In an aspect of the eighth embodiment, a substantial number of shortest dimensions of the solid portion are greater than or equal to about 5 microns and wherein a substantial number of longest dimensions of the solid portion are greater than or equal to about 2000 microns.

In an aspect of the eighth embodiment, a substantial number of shortest dimensions of the solid portion are greater than or equal to about 10 microns and wherein a substantial number of longest dimensions of the solid portion are greater than or equal to about 1000 microns.

In an aspect of the eighth embodiment, a substantial number of shortest dimensions of the solid portion are greater than or equal to about 10 microns and wherein a substantial number of longest dimensions of the solid portion are greater than or equal to about 400 microns.

In an aspect of the eighth embodiment, the solid portion includes silicone.

In an aspect of the eighth embodiment, the solid portion includes polyurethane.

In an aspect of the eighth embodiment, the solid portion includes a block copolymer.

In an aspect of the eighth embodiment, the solid portion includes a material selected from the group consisting of polytetrafluoroethylene, polyethylene-co-tetrafluoroethylene, polyolefin, polyester, and polycarbonate.

In an aspect of the eighth embodiment, the second domain includes a biostable material.

In an aspect of the eighth embodiment, the biostable material includes polyurethane and a hydrophilic polymer.

In an aspect of the eighth embodiment, the biostable material includes polyurethane and polyvinylpyrrolidone.

In an aspect of the eighth embodiment, the second domain includes greater than or equal to about 5 wt. % polyurethane and greater than or equal to about 45 wt. % polyvinylpyrrolidone.

In an aspect of the eighth embodiment, the second domain includes greater than or equal to about 20 wt. % polyurethane and greater than or equal to about 35 wt. % polyvinylpyrrolidone.

In an aspect of the eighth embodiment, the second domain includes polyurethane and about 27 wt. % polyvinylpyrrolidone.

In an aspect of the eighth embodiment, the second domain includes a silicone copolymer.

In an aspect of the eighth embodiment, the analyte includes glucose.

In a ninth embodiment, a method of measuring an analyte in a biological fluid is provided, the method including: providing an implantable device capable of accurate continuous analyte sensing, the implantable device including a housing and at least one sensor head, the housing including electronic circuitry, wherein the sensor head is operably connected to the electronic circuitry, the sensor head including a biointerface membrane, wherein the biointerface membrane includes: a first domain, wherein the first domain supports tissue ingrowth and interferes with barrier cell layer formation, wherein the first domain includes a plurality of interconnected cavities and a solid portion, and wherein a substantial number of the cavities are greater than or equal to about 90 microns in at least one dimension; and a second domain, the second domain allowing passage of an analyte, wherein the second domain is resistant to cellular attachment and is impermeable to cells and cell processes; implanting the device in a host; and measuring an analyte in a biological fluid.

In an aspect of the ninth embodiment, the step of implanting includes subcutaneously implanting.

In an aspect of the ninth embodiment, the step of implanting includes intramuscular implanting.

In an aspect of the ninth embodiment, the step of implanting includes intraperotoneal implanting.

In an aspect of the ninth embodiment, the step of implanting includes intrafascial implanting.

In an aspect of the ninth embodiment, the step of implanting includes implanting in an axillary region.

In an aspect of the ninth embodiment, the step of implanting includes implanting in soft tissue.

In an aspect of the ninth embodiment, the first domain includes a depth of greater than one cavity in three dimensions substantially throughout an entirety of the first domain.

In an aspect of the ninth embodiment, the cavities and a plurality of cavity interconnections are formed in a plurality of layers having different cavity dimensions.

In an aspect of the ninth embodiment, a substantial number of the cavities are greater than or equal to about 160 microns in at least one dimension.

In an aspect of the ninth embodiment, a substantial number of the cavities are greater than or equal to about 220 microns in at least one dimension.

In an aspect of the ninth embodiment, a substantial number of the cavities are greater than or equal to about 285 microns in at least one dimension.

In an aspect of the ninth embodiment, a substantial number of the cavities are greater than or equal to about 350 microns in at least one dimension.

In an aspect of the ninth embodiment, a substantial number of the cavities are greater than or equal to about 370 microns in at least one dimension.

In an aspect of the ninth embodiment, a substantial number of the cavities are from about 90 microns to about 370 microns in at least one dimension.

In an aspect of the ninth embodiment, a substantial number of the cavities are from about 220 microns to about 350 microns in at least one dimension.

In an aspect of the ninth embodiment, a substantial number of the cavities are from about 220 microns to about 285 microns in at least one dimension.

In an aspect of the ninth embodiment, a substantial number of the cavities are less than or equal to about 1000 microns in a longest dimension.

In an aspect of the ninth embodiment, a substantial number of the cavities are less than or equal to about 500 microns in a longest dimension.

In an aspect of the ninth embodiment, a substantial number of shortest dimensions of the solid portion are greater than or equal to about 5 microns and wherein a substantial number of longest dimensions of the solid portion are greater than or equal to about 2000 microns.

In an aspect of the ninth embodiment, a substantial number of shortest dimensions of the solid portion are greater than or equal to about 10 microns and wherein a substantial number of longest dimensions of the solid portion are greater than or equal to about 1000 microns.

In an aspect of the ninth embodiment, a substantial number of shortest dimensions of the solid portion are greater than or equal to about 10 microns and wherein a substantial number of longest dimensions of the solid portion are greater than or equal to about 400 microns.

In an aspect of the ninth embodiment, the solid portion includes silicone.

In an aspect of the ninth embodiment, the solid portion includes polyurethane.

In an aspect of the ninth embodiment, the solid portion includes a block copolymer.

In an aspect of the ninth embodiment, the solid portion includes a material selected from the group consisting of polytetrafluoroethylene, polyethylene-co-tetrafluoroethylene, polyolefin, polyester, and polycarbonate.

In an aspect of the ninth embodiment, the second domain includes a biostable material.

In an aspect of the ninth embodiment, the biostable material includes polyurethane and a hydrophilic polymer.

In an aspect of the ninth embodiment, the biostable material includes polyurethane and polyvinylpyrrolidone.

In an aspect of the ninth embodiment, the second domain includes greater than or equal to about 5 wt. % polyurethane and greater than or equal to about 45 wt. % polyvinylpyrrolidone.

In an aspect of the ninth embodiment, the second domain includes greater than or equal to about 20 wt. % polyurethane and greater than or equal to about 35 wt. % polyvinylpyrrolidone.

In an aspect of the ninth embodiment, the second domain includes polyurethane and about 27 wt. % polyvinylpyrrolidone.

In an aspect of the ninth embodiment, the second domain includes a silicone copolymer.

In an aspect of the ninth embodiment, the analyte includes glucose.

BRIEF DESCRIPTION OF THE DRAWINGS

FIG. 10A shows the average R-values (vertical axis) for each group versus time in days (horizontal axis). FIG. 10B is a graph that illustrates average sensor signal strength with respect to glucose concentration (i.e., sensitivity) on the vertical axis versus time in days on the horizontal axis for the ITS.

DETAILED DESCRIPTION

Figure 1:
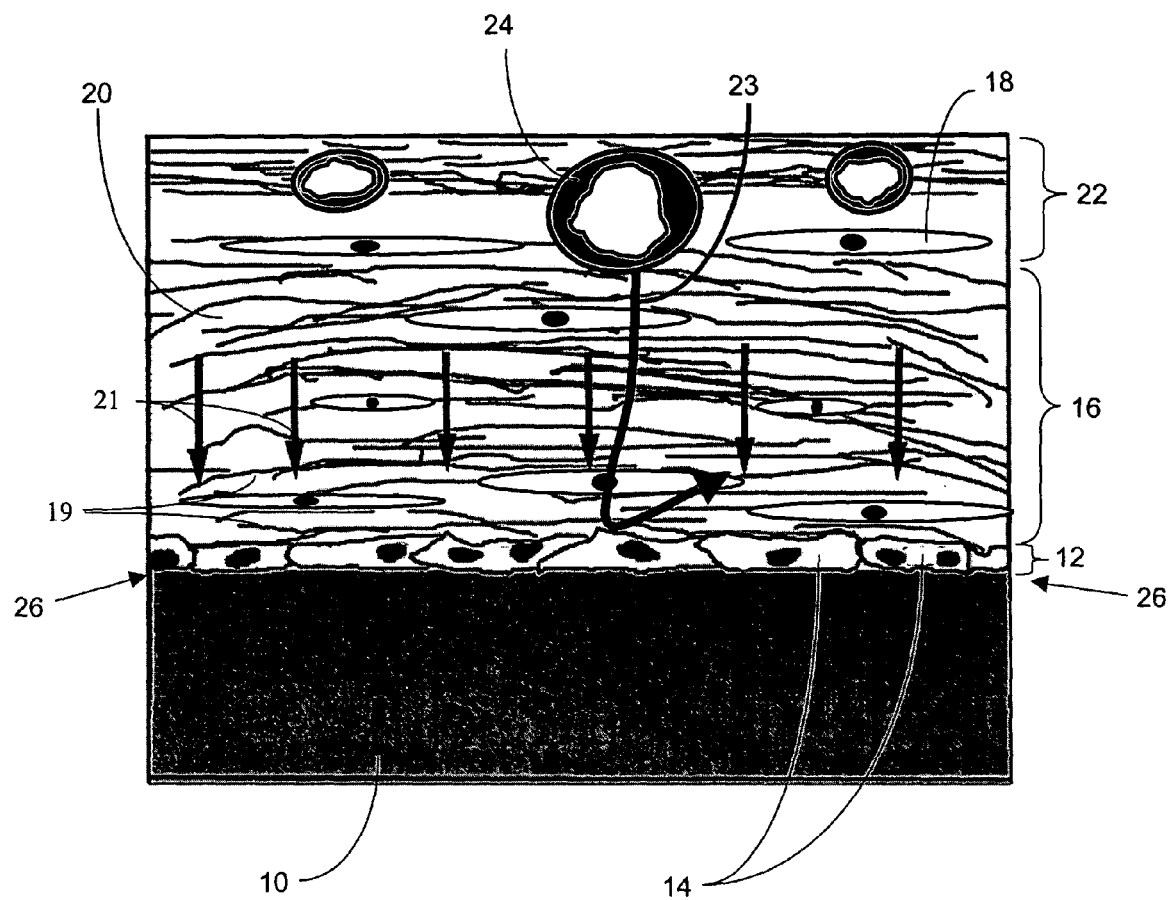
FIG. 1 is an illustration of classical three-layered foreign body response to a conventional synthetic membrane implanted under the skin.

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

Definitions

In order to facilitate an understanding of the preferred embodiments, a number of terms are defined below.

The term "biointerface membrane" as used herein is a broad term and is used in its ordinary sense, including, without limitation, a permeable membrane that functions as a device-tissue interface comprised of two or more domains. In some embodiments, the biointerface membrane is composed of two domains. The first domain supports tissue ingrowth, interferes with barrier cell layer formation, and includes an open cell configuration having cavities and a solid portion. The second domain is resistant to cellular attachment and impermeable to cells (e.g., macrophages). The biointerface membrane is made of biostable materials and can be constructed in layers, uniform or non-uniform gradients (i.e., anisotropic), or in a uniform or non-uniform cavity size configuration.

The term "domain" as used herein is a broad term and is used in its ordinary sense, including, without limitation, regions of the biointerface membrane that can be layers, uniform or non-uniform gradients (i.e., anisotropic) or provided as portions of the membrane.

The term "barrier cell layer" as used herein is a broad term and is used in its ordinary sense, including, without limitation, a cohesive monolayer of cells (e.g., macrophages and foreign body giant cells) that substantially block the transport of molecules across the second domain and/or membrane.

The term "cellular attachment", as used herein is a broad term and is used in its ordinary sense, including, without limitation, adhesion of cells and/or cell processes to a material at the molecular level, and/or attachment of cells and/or cell processes to micro- (or macro-) porous material surfaces. One example of a material used in the prior art that allows cellular attachment due to porous surfaces is the BIOPORE™ cell culture support marketed by Millipore (Bedford, Mass.) (see Brauker '330, supra).

The phrase "distal to" as used herein is a broad term and is used in its ordinary sense, including, without limitation, the spatial relationship between various elements in comparison to a particular point of reference. For example, some embodiments of a device include a biointerface membrane having a cell disruptive domain and a cell impermeable domain. If the sensor is deemed to be the point of reference and the cell disruptive domain is positioned farther from the sensor, then that domain is distal to the sensor.

The term "proximal to" as used herein is a broad term and is used in its ordinary sense, including, without limitation, the spatial relationship between various elements in comparison to a particular point of reference. For example, some embodiments of a device include a biointerface membrane having a cell disruptive domain and a cell impermeable domain. If the sensor is deemed to be the point of reference and the cell impermeable domain is positioned nearer to the sensor, then that domain is proximal to the sensor.

The term "cell processes" as used herein is a broad term and is used in its ordinary sense, including, without limitation, pseudopodia of a cell.

The term "solid portions" as used herein is a broad term and is used in its ordinary sense, including, without limitation, a solid material having a mechanical structure that demarcates the cavities, voids, or other non-solid portions.

The term "substantial" as used herein is a broad term and is used in its ordinary sense, including, without limitation, an amount greater than 50 percent.

The term "co-continuous" as used herein is a broad term and is used in its ordinary sense, including, without limitation, a solid portion wherein an unbroken curved line in three dimensions exists between any two points of the solid portion.

The term "biostable" as used herein is a broad term and is used in its ordinary sense, including, without limitation, materials that are relatively resistant to degradation by processes that are encountered in vivo.

The term "sensor" as used herein is a broad term and is used in its ordinary sense, including, without limitation, the component or region of a device by which an analyte can be quantified.

The term "analyte" as used herein is a broad term and is used in its ordinary sense, including, without limitation, to refer to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensor heads, devices, and methods is glucose. However, other analytes are contemplated as well, including but not limited to acarboxyprothrombin; acylcamitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; camitine; camosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobinopathies, A,S,C,E, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17 alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenyloin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani, leptospira*, measles/mumps/rubella, *Mycobacterium leprae, Mycoplasma pneumoniae, Myoglobin, Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni, Toxoplasma gondii, Trepenoma pallidium, Trypanosoma cruzi*/rangeli, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), and 5-hydroxyindoleacetic acid (FHIAA).

The terms. "operably connected" and "operably linked" as used herein are broad terms and are used in their ordinary sense, including, without limitation, one or more components being linked to another component(s) in a manner that allows transmission of signals between the components. For example, one or more electrodes can be used to detect the amount of analyte in a sample and convert that information into a signal; the signal can then be transmitted to a circuit. In this case, the electrode is "operably linked" to the electronic circuitry.

The term "electronic circuitry" as used herein is a broad term and is used in its ordinary sense, including, without limitation, the components of a device required to process biological information obtained from a host. In the case of an analyte-measuring device, the biological information is obtained by a sensor regarding a particular analyte in a biological fluid, thereby providing data regarding the amount of that analyte in the fluid. U.S. Pat. Nos. 4,757,022, 5,497,772 and 4,787,398 describe suitable electronic circuit means that can be utilized with devices including the biointerface membrane of a preferred embodiment.

The phrase "member for determining the amount of glucose in a biological sample" as used herein is a broad term and is used in its ordinary sense, including, without limitation, any mechanism (e.g., enzymatic or non-enzymatic) by which glucose can be quantified. For example, some embodiments utilize a membrane that contains glucose oxidase that catalyzes the conversion of oxygen and glucose to hydrogen peroxide and gluconate:

Because for each glucose molecule metabolized, there is a proportional change in the co-reactant $O_2$ and the product $H_2O_2$, one can monitor the current change in either the co-reactant or the product to determine glucose concentration.

The term "host" as used herein is a broad term and is used in its ordinary sense, including, without limitation, mammals, particularly humans.

The term "R-value" as used herein is a broad term and is used in its ordinary sense, including, without limitation, one conventional way of summarizing the correlation (or association) between two types of data; that is, a statement of what residuals (e.g., root mean square deviations) are to be expected if the data are fitted to a straight line by the a regression.

The phrase "continuous (or continual) analyte sensing" as used herein is a broad term and is used in its ordinary sense, including, without limitation, the period in which monitoring of analyte concentration is continuously, continually, and or intermittently (but regularly) performed, for example, about every 5 to 10 minutes.

The term "sensor head" as used herein is a broad term and is used in its ordinary sense, including, without limitation, the region of a monitoring device responsible for the detection of a particular analyte. The sensor head generally comprises a non-conductive body, a working electrode (anode), a reference electrode and a counter electrode (cathode) passing through and secured within the body forming an electrochemically reactive surface at one location on the body and an electronic connective means at another location on the body, and a multi-region membrane affixed to the body and covering the electrochemically reactive surface. The counter electrode has a greater electrochemically reactive surface area than the working electrode. During general operation of the sensor a biological sample (e.g., blood or interstitial fluid) or a portion thereof contacts (directly or after passage through one or more membranes or domains) an enzyme (e.g., glucose oxidase); the reaction of the biological sample (or portion thereof) results in the formation of reaction products that allow a determination of the analyte (e.g., glucose) level in the biological sample. In some embodiments, the multi-region membrane further comprises an enzyme domain (e.g., and enzyme layer), and an electrolyte phase (i.e., a free-flowing liquid phase comprising an electrolyte-containing fluid described further below).

The term "electrochemically reactive surface" as used herein is a broad term and is used in its ordinary sense, including, without limitation, the surface of an electrode where an electrochemical reaction takes place. In the case of the working electrode, the hydrogen peroxide produced by the enzyme catalyzed reaction of the analyte being detected reacts creating a measurable electronic current (e.g., detection of glucose analyte utilizing glucose oxidase produces $H_2O_2$ peroxide as a by product, $H_2O_2$ reacts with the surface of the working electrode producing two protons ($2H^+$), two electrons ($2e^-$) and one molecule of oxygen ($O_2$) which produces the electronic current being detected). In the case of the counter electrode, a reducible species, e.g., $O_2$ is reduced at the electrode surface in order to balance the current being generated by the working electrode.

The term "electronic connection" as used herein is a broad term and is used in its ordinary sense, including, without limitation, any electronic connection known to those in the art that can be utilized to interface the sensor head electrodes with the electronic circuitry of a device such as mechanical (e.g., pin and socket) or soldered.

The term "sensing membrane" as used herein is a broad term and is used in its ordinary sense, including, without limitation, a permeable or semi-permeable membrane that can comprise one or more domains and constructed of materials of a few microns thickness or more, which are permeable to oxygen and may or may not be permeable to an analyte of interest. In one example, the sensing membrane comprises an immobilized glucose oxidase enzyme, which enables an electrochemical reaction to occur to measure a concentration of glucose.

The phrase "distal" and "distant from" as used herein are broad terms and are used in their ordinary sense, including, without limitation, the spatial relationship between various elements in comparison to a particular point of reference. For example, some embodiments of a biological fluid measuring device comprise a multi-region membrane that can be comprised of a number of domains. If the electrodes of the sensor head are deemed to be the point of reference, and one of the multi-region membrane domains is positioned farther from the electrodes, than that domain is distant from the electrodes.

The term "oxygen antenna domain" as used herein is a broad term and is used in its ordinary sense, including, without limitation, a domain composed of a material that has higher oxygen solubility than aqueous media so that it concentrates oxygen from the biological fluid surrounding the biointerface membrane. The domain can then act as an oxygen reservoir during times of minimal oxygen need and has the capacity to provide on demand a higher oxygen gradient to facilitate oxygen transport across the membrane. This enhances function in the enzyme reaction domain and at the counter electrode surface when glucose conversion to hydrogen peroxide in the enzyme domain consumes oxygen from the surrounding domains. Thus, this ability of the oxygen antenna domain to apply a higher flux of oxygen to critical domains when needed improves overall sensor function.

The following abbreviations apply herein: Eq and Eqs (equivalents); mEq (milliequivalents); M (molar); mM (millimolar) μM (micromolar); N (Normal); mol (moles); mmol (millimoles); μmol (micromoles); nmol (nanomoles); g (grams); mg (milligrams); μg (micrograms); Kg (kilograms); L (liters); mL (milliliters); dL (deciliters); μL (microliters); cm (centimeters); mm (millimeters); μm (micrometers); nm (nanometers); h and hr (hours); min. (minutes); s and sec. (seconds); and ° C. (degrees Centigrade).

Overview

Biointerface membranes and their use with implantable devices in a biological fluid are employed in the preferred embodiments. For example, the biointerface membranes can be utilized with implantable devices and methods for monitoring and determining analyte levels in a biological fluid, such as measurement of glucose levels for individuals having diabetes.

Although much of the description that follows is directed at glucose monitoring devices including the described biointerface membranes and methods for their use, these biointerface membranes are not limited to use in devices that measure or monitor glucose. Rather, these biointerface membranes can be applied to a variety of devices, including for example, those that detect and quantify other analytes present in biological fluids (including, but not limited to, cholesterol, amino acids, and lactate), especially those analytes that are substrates for oxidase enzymes (U.S. Pat. No. 4,703,756), cell transplantation devices (U.S. Pat. Nos. 6,015,572, 5,964,745, and 6,083,523), drug delivery devices (U.S. Pat. Nos. 5,458,631, 5,820,589, and 5,972,369) and electrical delivery and/or measuring devices such as implantable pulse generation cardiac pacing devices (U.S. Pat. Nos. 6,157,860, 5,782,880, and 5,207,218), electrocardiogram device (U.S. Pat. Nos. 4,625,730 and 5,987,352) and electrical nerve stimulating devices (U.S. Pat. Nos. 6,175,767, 6,055,456, and 4,940,065). One further example includes not only utilizing the biointerface membranes for transplanted cells, e.g., transplanted genetic engineered cells of Langerhans, either allo, auto or xeno type as pancreatic beta cells to increase the diffusion of nutrients to the islets, but additionally utilizing a biosensor to sense glucose in the tissues of the patient to monitor the viability of the implanted cells.

Implantable devices for detecting analyte concentrations in a biological system can utilize the biointerface membranes of the preferred embodiments to interfere with the formation of a barrier cell layer, thereby assuring that the sensor receives analyte concentrations representative of that in the vasculature. Drug delivery devices can utilize the biointerface membranes of the preferred embodiments to protect the drug housed within the device from host inflammatory or immune cells that might potentially damage or destroy the drug. In addition, the biointerface membrane prevents the formation of a barrier cell layer that might interfere with proper dispensing of drug from the device for treatment of the host. Correspondingly, cell transplantation devices can utilize the biointerface membranes of the preferred embodiments to protect the transplanted cells from attack by the host inflammatory or immune response cells while simultaneously allowing nutrients as well as other biologically active molecules needed by the cells for survival to diffuse through the membrane.

The materials contemplated for use in preparing the biointerface membrane also eliminate or significantly delay biodegradation. This is important for devices that continuously measure analyte concentrations, deliver drugs, and/or for cell transplantation devices, for example. As one example, in a glucose-measuring device, the electrode surfaces of the glucose sensor are in contact with (or operably connected with) a thin electrolyte phase, which in turn is covered by a membrane that contains an enzyme, e.g., glucose oxidase, and a polymer system, such as described in U.S. Published Patent Application 2003/0032874, which is incorporated herein in its entirety. In this example, the biointerface membrane covers this enzyme membrane and serves, in part, to protect the sensor from external forces and factors that can result in biodegradation. By significantly delaying biodegradation at the sensor, accurate data can be collected over long periods of time (e.g., months to years). Correspondingly, biodegradation of the biointerface membrane of implantable cell transplantation devices and drug delivery devices can allow host inflammatory and immune cells to enter these devices, thereby compromising long-term function.

Nature of the Foreign Body Response

Devices and probes that are implanted into subcutaneous tissue typically elicit a foreign body response (FBR), which forms a foreign body capsule (FBC), as part of the body's response to the introduction of a foreign material. That is, implantation of a device (e.g., a glucose sensor) results in an acute inflammatory reaction followed by building of fibrotic tissue such as described in more detail in the background section, above. Ultimately, a mature FBC including primarily a vascular fibrous tissue forms around the device. See Shanker and Greisler, Inflammation and Biomaterials in Greco RS, ed., "Implantation Biology: The Host Response and Biomedical Devices" pp 68–80, CRC Press (1994).

The FBC around conventional membranes precludes the transport of analytes across the device-tissue interface. Thus, a collection of reliable, continuous information was precluded because it was previously believed that the FBC isolates the sensor of the implanted device in a capsule containing fluid that does not mimic the levels of analytes (e.g., glucose and oxygen) in the body's vasculature. Similarly, the composition of a FBC can prevent stabilization of the implanted device, contributing to motion artifact that also renders unreliable results. Thus, conventionally, it has been the practice of those skilled in the art to attempt to minimize FBR formation by, for example, using a short-lived needle geometry or sensor coatings to minimize the foreign body reaction.

In contrast to conventional practice, it has been recognized that FBC formation is the dominant event surrounding long-term implantation of any sensor and is managed to support rather than hinder or block sensor performance. It has been observed that during the early periods following implantation of an analyte-sensing device, particularly a glucose sensing device, glucose sensors function well. However, after a few days to two or more weeks of implantation, these devices lose their function. See, e.g., U.S. Pat. No. 5,791,344 and Gross et al. and "Performance Evaluation of the MiniMed Continuous Monitoring System During Patient home Use," Diabetes Technology and Therapeutics, (2000) 2(1):49–56, which have reported a glucose oxidase sensor (that has been approved for use in humans by the Food and Drug Administration) that functioned well for several days following implantation but loses function quickly after 3 days. These results suggest that there is sufficient vascularization and, therefore, perfusion of oxygen and glucose to support the function of an implanted glucose sensor for the first few days following implantation. New blood vessel formation is clearly not needed for the function of a glucose oxidase mediated electrochemical sensor implanted in the subcutaneous tissue for at least several days after implantation.

After several days, however, it is believed that this lack of sensor function is most likely due to cells, such as polymorphonuclear cells and monocytes that migrate to the wound site during the first few days after implantation. These cells consume local glucose and oxygen. If there is an overabundance of such cells, they can deplete the glucose and/or oxygen before it is able to reach the sensor enzyme layer, thereby reducing the sensitivity of the device or rendering it non-functional. Further inhibition of device function may be due to inflammatory response cells (e.g., macrophages) that associate (e.g., overgrow at the interface) with the membrane of the device and physically block the transport of glucose into the device (i.e., barrier cell layer).

Additionally, these inflammatory cells can biodegrade many artificial biomaterials (some of which were, until recently, considered nonbiodegradable). When activated by a foreign body, tissue macrophages degranulate, releasing hypochlorite (bleach) and other oxidative species. Hypochlorite and other oxidative species are known to break down a variety of polymers.

In order to overcome the problems associated with conventional membranes, the preferred embodiments employ biointerface membrane architectures that promote vascularization within the membrane and interfere with barrier cell layer formation. These embodiments provide a robust membrane that is suitable for long-term implantation and long-term analyte transport in vivo. Additionally, the membranes can be used with a variety of implantable devices (e.g., analyte measuring devices, particularly glucose measuring devices, cell transplantation devices, drug delivery devices, and electrical signal delivery and measuring devices). For example, in some embodiments of a glucose-monitoring device, the sensor interface, which refers to that region where a biological sample contacts (directly or after passage through one or more membranes or layers) an enzyme (e.g., glucose oxidase), can include a sensing membrane that has different domains and/or layers that can cover and protect an underlying enzyme membrane and the electrodes of an implantable analyte-measuring device.

In general, the biointerface membranes of the preferred embodiments prevent direct contact of the biological fluid sample with the an implanted device and permit only selected substances (e.g., analytes) of the fluid to pass therethrough for reaction in the immobilized enzyme domain. The biointerface membranes of preferred embodiments are robust, biostable, and prevent barrier cell formation. The characteristics of this biointerface membrane are now discussed in more detail.

Biointerface Membrane

The biointerface membrane of the preferred embodiments comprises two or more domains. A first domain comprises an architecture, including a cavity size, configuration, and overall thickness that encourages vascular tissue ingrowth and disrupts barrier cell formation in vivo, and a second domain that comprises a cell impermeable layer that is resistant to cellular attachment and has a robust interface that does not suffer from disadvantages of the prior art, such as attachment of barrier cells and delamination of the domains.

Figure 3A:
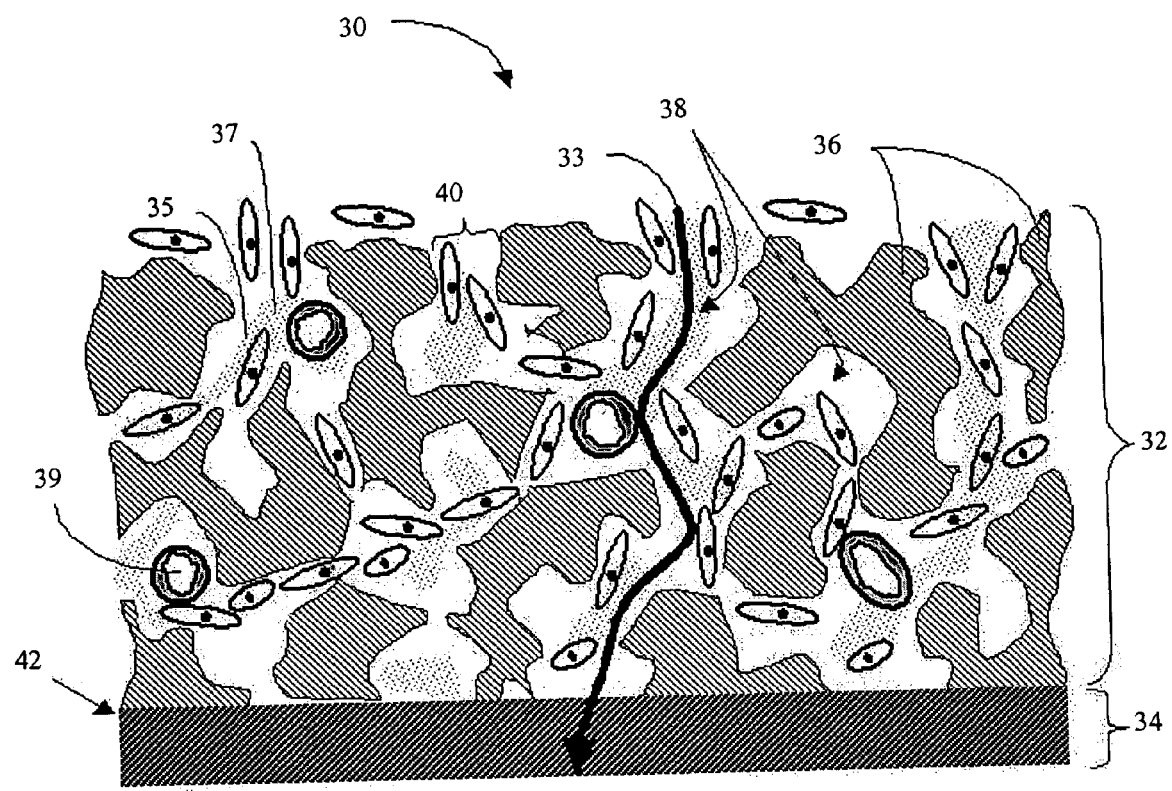
FIG. 3A is an illustration of a membrane in one embodiment that enables vascularization of the first domain without cell adhesion to the second domain.

FIG. 3A is a cross-sectional schematic view of a membrane 30 in vivo in one exemplary embodiment, wherein the membrane comprises a first domain 32 and second domain 34. The architecture of the membrane provides a robust long-term implantable membrane that allows the transport of analytes through vascularized tissue ingrowth without the formation of a barrier cell layer.

The first domain 32 comprises a solid portion 36 and a plurality of interconnected three-dimensional cavities 38 formed therein. The cavities 38 have sufficient size and structure to allow invasive cells, such as fibroblasts 35, fibrous matrix 37, and blood vessels 39 to completely enter into the apertures 40 that define the entryway into each cavity 38, and to pass through the interconnected cavities toward the interface 42 between the first and second domain. The cavities comprise an architecture that encourages the ingrowth of vascular tissue in vivo as indicated by the blood vessels 39 formed throughout the cavities. Because of the vascularization within the cavities, solutes 33 (e.g., oxygen, glucose and other analytes) can pass through the first domain with relative ease and/or the diffusion distance (i.e., distance that the glucose diffuses) can be reduced.

Figure 2:
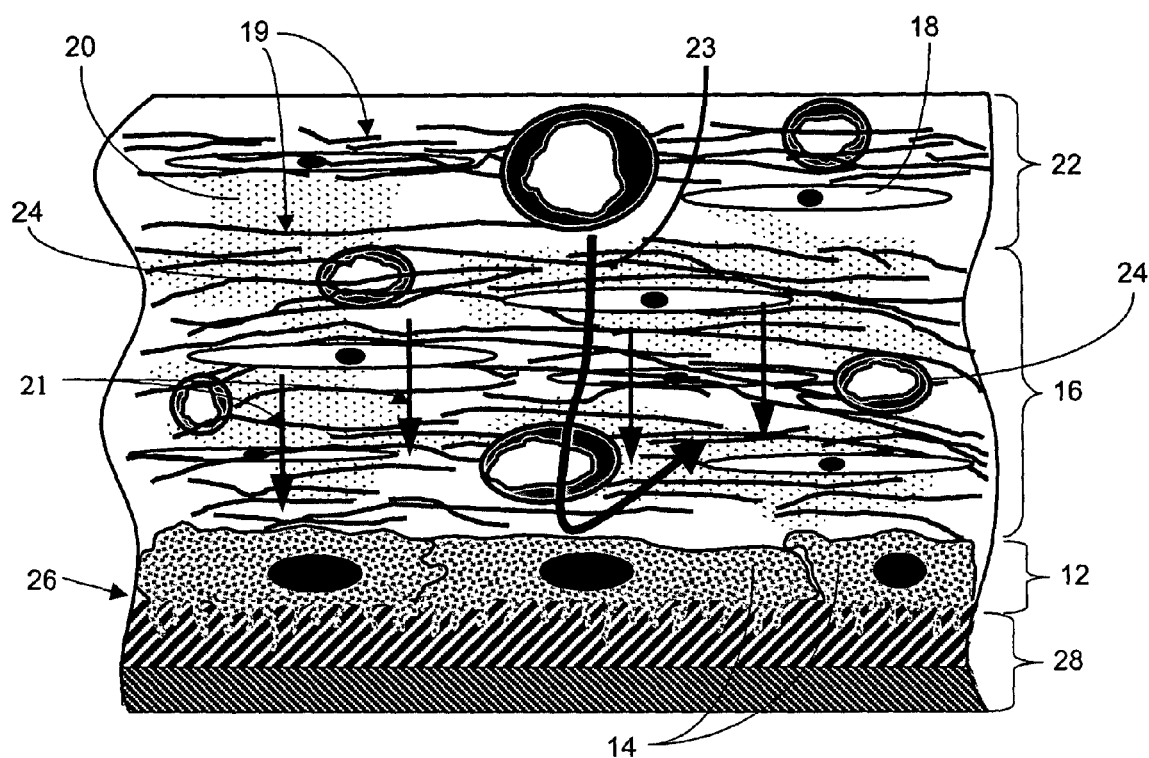
FIG. 2 is an illustration of a conventional membrane enabling increased neovascularization within the intermediary layer of the foreign body response, however showing a barrier cell layer that limits the transport of analytes.

The second domain 34 comprises a cell impermeable layer that is resistant to cellular attachment and thus provides another mechanism for resisting barrier cell layer formation (indicated in FIG. 3A by less macrophages and/or giant cells at the interface 42 between the first and second domains). Because the second domain 34 is resistant to cellular attachment and barrier cell layer formation, the transport of solutes such as described above can also pass through with relative ease without blockage by barrier cells as seen in the prior art (FIGS. 1 and 2).

Architecture of the First Domain

The first domain of the membrane includes an architecture that supports tissue ingrowth, disrupts contractile forces typically found in a foreign body response, encourages vascularity within the membrane, and disrupts the formation of a barrier cell layer. The first domain, which can also be referred to as the cell disruptive domain, comprises an open-celled configuration that has interconnected cavities and solid portions. The distribution of the solid portion and cavities of the first domain includes a substantially co-continuous solid domain and includes more than one cavity in three dimensions substantially throughout the entirety of the first domain. Cells can enter into the cavities, however they cannot travel through or wholly exist within the solid portions. The cavities allow most substances to pass through, including, e.g., cells and molecules.

Figure 3B:
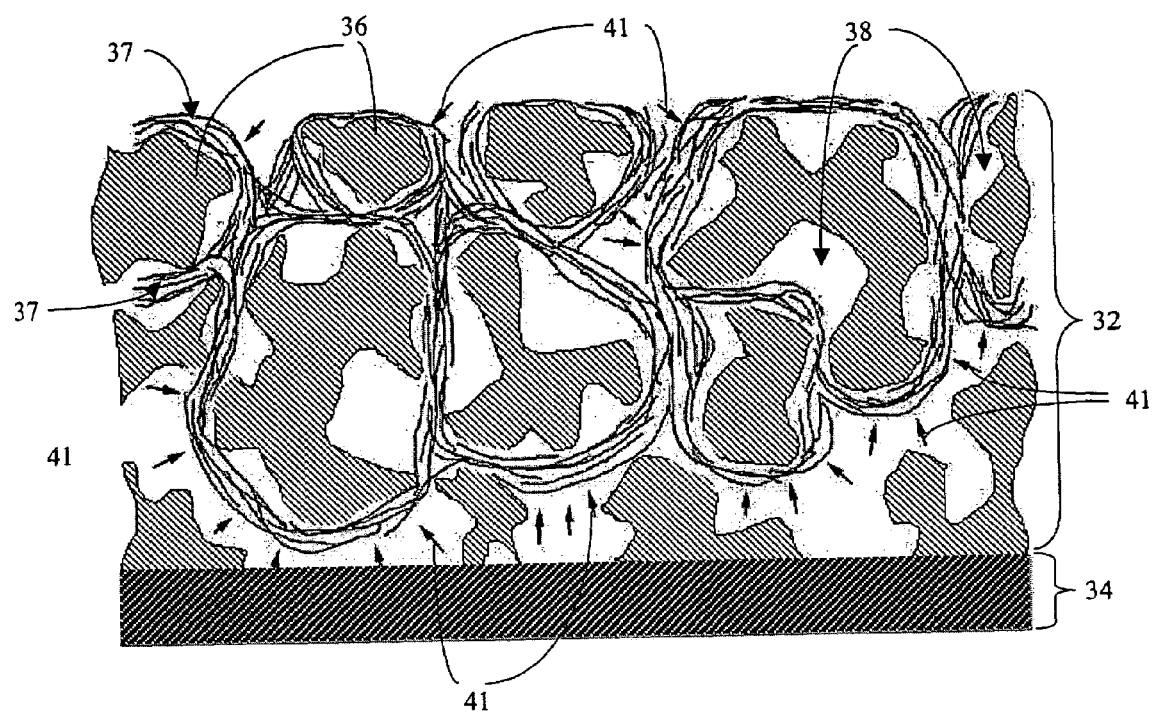
FIG. 3B is an illustration of the membrane of FIG. 3A showing contractile forces cause by the fibrous tissue of the FBR.

Reference is now made to FIG. 3B, which an illustration of the membrane of FIG. 3A, showing contractile forces caused by the fibrous tissue (e.g., from the fibroblasts and fibrous matrix) of the FBR. Particularly, the architecture of the first domain, including the cavity interconnectivity and multiple-cavity depth, (i.e., two or more cavities in three dimensions throughout a substantial portion of the first domain) can affect the tissue contracture that typically occurs around a foreign body.

It is noted that a contraction of the FBC around the device as a whole produces downward forces (not shown) on the device, which can be helpful in reducing motion artifacts such as described with reference to copending U.S. patent application Ser. No. 10/646,333 filed on Aug. 22, 2003, and entitled "OPTIMIZED SENSOR GEOMETRY FOR AN IMPLANTABLE GLUCOSE SENSOR," which is incorporated herein in its entirety by reference. However, the architecture of the first domain described herein, including the interconnected cavities and solid portion, are advantageous because the contractile forces caused by the downward tissue contracture that can otherwise cause cells to flatten against the device and occlude the transport of analytes, is instead translated to, disrupted by, and/or counteracted by the forces 41 that contract around the solid portions 36 (e.g., throughout the interconnected cavities 38) away from the device. That is, the architecture of the solid portions 36 and cavities 38 of the first domain cause contractile forces 41 to disperse away from the interface between the first domain 32 and second domain 34. Without the organized contracture of fibrous tissue toward the tissue-device interface typically found in a FBC, macrophages and foreign body giant cells substantially do not form a monolayer of cohesive cells (i.e., barrier cell layer) and therefore the transport of molecules across the second domain and/or membrane is substantially not blocked (indicated by free transport of analyte 33 through the first and second domains in FIG. 3A).

Figure 4:
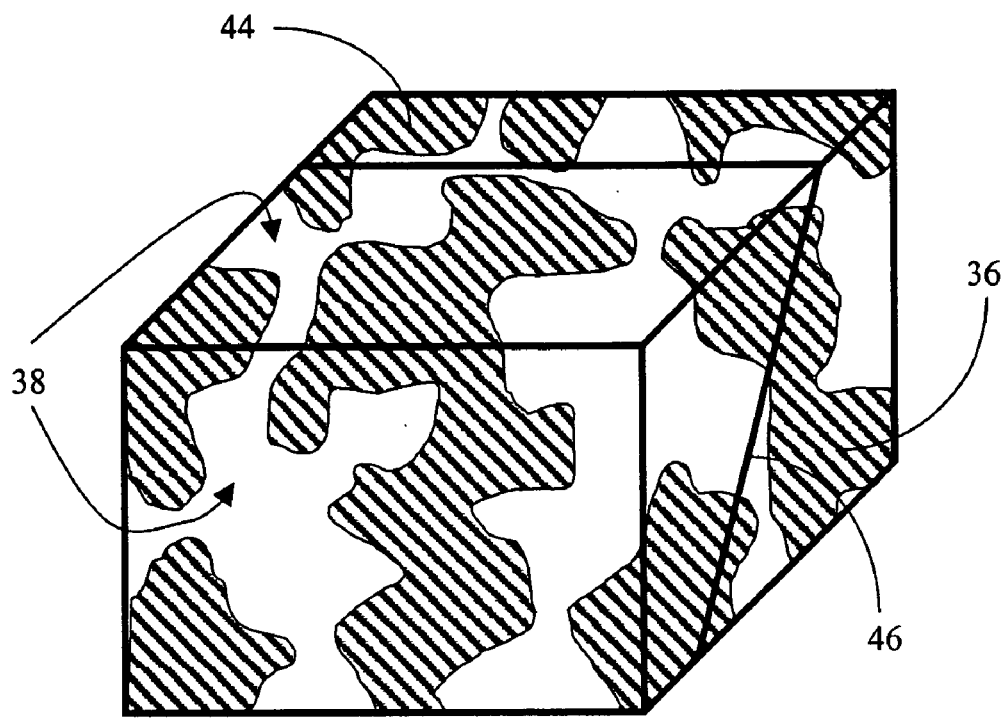
FIG. 4 is a three-dimensional section of the first domain in the embodiment of FIGS. 3A and 3B, which shows the solid portions and cavities and their dimensions.
Figure 5:
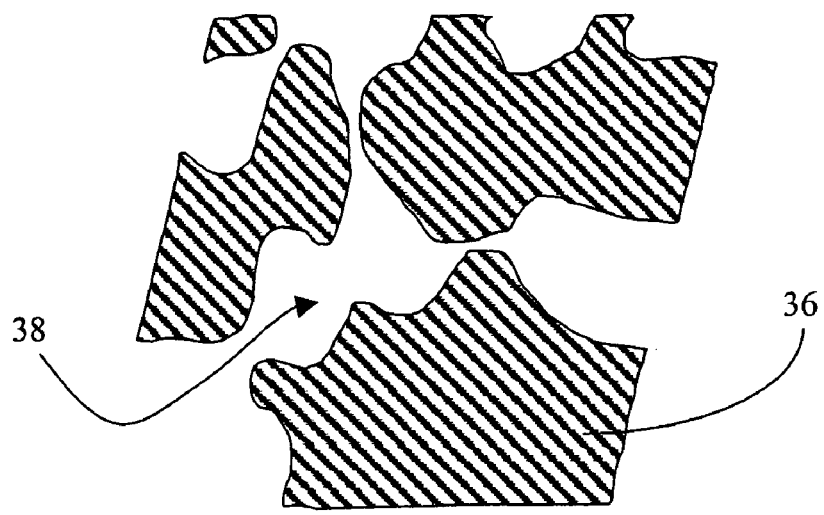
FIG. 5 is a two-dimensional cross-section of the first domain, taken at a plane through the three-dimensional section of FIG. 4, which shows the solid portions and cavities and their dimensions.

Reference is now made to FIGS. 4 and 5 in order to further describe the architecture, including configuration and dimensions of solid portions 36 and cavities 38. FIG. 4 is a three-dimensional section of the first domain in the embodiment of FIGS. 3A and 3B, which shows the configuration and dimensions of solid portions and cavities. FIG. 5 is a two-dimensional cross-section of the first domain taken at plane 44 in FIG. 4, which also shows the configuration and dimensions of solid portions and cavities.

Numerous methods have been contemplated for manufacturing the first domain in order to create the preferred architecture (e.g., dimensions and overall structure). In some embodiments, the first domain can be manufactured by forming particles (e.g., sugar, salt, or other natural or synthetic uniform or non-uniform particles) in a mold, wherein the particles have shapes and sizes substantially corresponding to the desired cavity dimensions. Most often, the particles are made to coalesce to provide the desired interconnectivity between the cavities. The desired material for the solid portion can be introduced into the mold using methods common in the art of polymer processing, for example injecting, pressing, vacuuming, or pouring. After the solid portion material is cured or solidified, the coalesced particles are then dissolved, melted, etched, or otherwise removed leaving interconnecting cavities within the solid portion. It is noted in such embodiments, that sieving can be used to determine the dimensions of the particles (which substantially correspond to the dimensions of resulting cavities). In sieving (also known as screening), the particles can be added to the sieve and then shaken to produce an "overs" and an "unders." The overs are the particles that remain on the screen and the unders are the particles that pass through the screen. Although one example of determining particle size has been described, other methods known in the art can be utilized, for example air classifiers (e.g., applying opposing air flows and centrifugal forces to separate particles down to 2 microns) can be used to determine particle size when particles are smaller than 100 microns.

Accordingly, the nominal cavity size of the cavities 38 of the first domain can be substantially defined by the particle size used in creating the cavities. It is noted that in some embodiments, the particles used to form the cavities can be substantially spherical, thus the dimensions below describe a diameter of the particle and/or a diameter of the cavity. In some alternative embodiments, the particles used to form the cavities can be non-spherical (e.g., rectangular, square, diamond, or other geometric or non-geometric shapes), thus the dimensions below describe one dimension (e.g., shortest, average, or longest, for example) of the particle and/or cavity.

In some embodiments, a variety of different particle sizes can be used in the manufacture of the first domain. In some embodiments, the dimensions of the particles can be somewhat smaller or larger than the dimensions of the resulting cavities due to dissolution or other precipitation that can occurring during the manufacturing process, for example.

In some embodiments, a substantial number of the cavities are greater than or equal to about 90 microns in one dimension; in other embodiments, a substantial number of the cavities are greater than or equal to about 160 microns in one dimension, greater than or equal to about 220 microns in one dimension, greater than or equal to about 285 microns in one dimension, greater than or equal to about 350 microns in one dimension, or greater than or equal to about 370 microns in one dimension.

In some embodiments, a substantial number of the cavities are less than or equal to about 1000 microns in one dimension. In other embodiments, a substantial number of the cavities are less than or equal to 500 microns in one dimension. In some embodiments, a substantial number of the cavities can be from about 220 to about 370 microns in one dimension, from about 220 to about 350 microns in one dimension, and from about 220 to about 285 microns in one dimension.

In one alternative embodiment, wherein a substantial number of cavities are greater than or equal to about 90 microns in one dimension, there can be additional cavities that are less than or equal to about 90 microns in their shortest dimension interspersed therein. In another alternative embodiment, wherein a substantial number of cavities are greater than or equal to about 90 microns in one dimension, cavity dimensions can be gradually increased or decreased progressively through the layer, including some cavities that are less than or equal to about 90 dimensions in one dimension. Additionally, in further alternative embodiments, an additional layer can be added that comprises a substantial number of cavities that are less than about 90 microns in one dimension (e.g., an ePTFE layer); in these alternative embodiments, the layer can be disposed above, below, or within the first domain of the membrane, for example.

Regarding the solid portion(s) of the first domain, a substantial number of the shortest dimensions are greater than or equal to about 5 microns and a substantial number of the longest dimensions are less than or equal to about 2000 microns in one embodiment. In other embodiments, the solid portion is less than or equal to about 10 microns in a substantial number of the shortest dimensions and less than or equal to about 1000 microns in a substantial number of the longest dimensions. In further embodiments, the solid portion is less than or equal to about 10 microns in a substantial number of the shortest dimensions and less than or equal to about 400 microns in a substantial number of the longest dimensions. However, the solid portion in other embodiments can have larger or smaller dimensions.

With regard to the above-described dimensions of the solid portion, the preferred structure has been found to provide the mechanical strength and overall structural integrity to withstand the natural biological and mechanical stresses that occur long term in vivo. It is noted that the optimum dimensions and overall structural integrity of the membrane will vary with the parameters of the device that it can support. For example, if the membrane is employed with a glucose sensor, the mechanical requirements of the membrane will be greater for devices having greater overall weight and surface area as compared to those that are relatively smaller.

With regard to the depth of cavities, improved vascular tissue ingrowth has been shown when the first domain has a thickness that enables a depth of at least two cavities throughout a substantial portion thereof. In other words, improved vascularization results at least in part from multi-layered interconnectivity of the cavities such as in the preferred embodiments, as compared to a surface topography such as seen in the prior art (e.g., wherein the first domain has a depth of only one cavity throughout a substantial portion thereof). The multi-layered interconnectivity of the cavities enables vascularized tissue to grow into various layers of cavities in a manner that provides mechanical anchoring of the device with the surrounding tissue. Such anchoring resists movement that can occur in vivo, which results in less sheer stresses and scar tissue formation, for example. Similar to the description of the optimum dimensions above, it is noted that the optimum depth (i.e., number) of cavities will vary with the parameters of the device that it can support. For example, if the membrane is employed with a glucose sensor, the anchoring that can be required of the membrane will be greater for devices having greater overall weight and surface area as compared to those that are relatively smaller.

With regard to the overall thickness of the first domain, the thickness can be optimized for decreased time-to-vascularize in vivo, that is, vascular tissue ingrowth can occur somewhat faster with a membrane that has a thin first domain as compared to a membrane that has a relatively thicker first domain. It is noted that decreased time-to-vascularize results in faster stabilization and functionality of the biointerface in vivo. For example in a subcutaneous implantable glucose sensor, consistent and increasing functionality of the device is at least in part a function of consistent and stable glucose transport across the biointerface membrane, which is at least in part a function of the vascularization thereof; thus quicker start-up time and/or shortened time lag (e.g., the diffusion path of the glucose through the membrane can be reduced) can be accomplished by decreasing the thickness of the membrane (i.e., first domain).

In some embodiments, thickness of the first domain can be between about 300 microns and about 2000 microns. In one embodiment, the thickness of the first domain is about 800 microns. However, in some alternative embodiments a thinner or thicker cell disruptive domain (i.e., first domain) can be desired.

It is noted that the above described membrane properties (e.g., dimensions of the solid portion and cavities, and overall the thickness) are in contrast to the prior art. For example, it was previously believed that substantially smaller pore sizes (e.g., from 0.6 to 20 microns such as described in the Brauker '330 patent) were required for analyte transport to occur in vivo. Additionally, greater overall thickness of the biointerface membrane with larger pore sizes was seen as a hindrance to analyte transport in the prior art (e.g., Brauker '330 patent); thus, it was previously believed that the thickness necessary to support the cavity size and configuration of preferred embodiments would be a barrier to sufficient vascularization and analyte transport in vivo. In fact, larger cavity sizes, and accordingly large membrane thickness, were believed to be appropriate mostly for tissue anchoring in prosthetic devices such as breast implants, which are not concerned with the transport of analytes (e.g., Seare, supra).

It is noted that although some short-term success was seen in the small pore size range of the prior art (e.g., 0.6 to 20 microns), significant problems have been found with this pore size long term in vivo due at least in part to a lack of mechanical robustness. In contrast to the prior art, the preferred embodiments employ a range of relatively larger cavity sizes (e.g., greater than or equal to about 90 microns), which was not previously believed to be suitable for soft tissue applications requiring analyte transport. However, the preferred embodiments have shown the tissue ingrowth, analyte transport, and mechanical robustness in vivo to support long-term implantation for devices that require analyte transport across the membrane.

In some embodiments, the solid portion can comprise one or more materials selected from the group comprising: silicone, polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, polysulfones and block copolymers thereof including, for example, di-block, tri-block, alternating, random and graft copolymers. In some embodiments, the material selected for the first domain is an elastomeric material (e.g., silicone), which is able to absorb stresses that can occur in vivo, so that sheer and other environmental forces are significantly minimized at the second domain. Additionally, elastomeric materials with a memory of the original configuration can withstand greater stresses without effecting the configuration, and thus the function of the device.

Although one method of manufacturing porous domains is described above, a variety of methods known to one of ordinary skill in the art could be employed to create the structure of preferred embodiments. For example, Roy (U.S. Pat. No. 3,929,971) discloses a method of making a synthetic membrane having a porous microstructure made by converting calcium carbonate coral materials to hydroxyapatite while at the same time retaining the unique microstructure of the coral material. As another example, Pekkarinen et al. (U.S. Pat. No. 6,520,997) discloses a photolithographic process for creating a porous membrane.

Architecture of the Second Domain

The second (innermost) domain of the membrane is non-adhesive for cells and is impermeable to cells, which is in contrast to the membranes of the prior art (e.g., Brauker et al. (supra)). For example, the cell-impenetrable membrane (of Brauker et al.) is derived from a membrane known as BIOPORE™, marketed as a cell culture support by Millipore (Bedford, Mass.). In the presence of certain extra cellular matrix molecules, which are present in vivo, many cell types are able to strongly adhere to this membrane, making it incapable of serving as a non-adhesive domain. Furthermore, since such prior art membranes allow adherence of cells to the innermost layer of the membrane, they promote barrier cell layer formation that decreases the membrane's ability to transport molecules (e.g., analytes) across the device-tissue interface. Moreover, when these cells multiply, they ultimately apply pressure between the membrane layers, resulting in delamination and distortion of the layers and catastrophic failure of the membrane.

Reference is again made to FIGS. 3A and 3B, which illustrate the second domain of the membrane that is resistant to cellular attachment, impermeable to cells, and composed of a biostable material. Because the second domain is resistant to cellular attachment (e.g., macrophages are kept a sufficient distance from the enzyme active membrane), hypochlorite and other oxidizing species are short-lived chemical species in vivo, and biodegradation does not occur; additionally, the materials (e.g., polycarbonate-based polyurethanes, silicones, and other such materials described herein) are resistant to the effects of these oxidative species and have been termed biodurable.

In one embodiment, the second domain is comprised of polyurethane and a hydrophilic polymer. In another embodiment, the hydrophilic polymer is polyvinylpyrrolidone. In another embodiment, the second domain is polyurethane comprising not less than 5 weight percent polyvinylpyrrolidone and not more than 45 weight percent polyvinylpyrrolidone. In another embodiment, the second domain comprises not less than 20 weight percent polyvinylpyrrolidone and not more than 35 weight percent polyvinylpyrrolidone. In another embodiment the second domain is polyurethane comprising about 27-weight percent polyvinylpyrrolidone. In certain embodiments, however, the second domain can comprise less than 5 weight percent or more than 45 weight percent polyvinylpyrrolidone.

In alternative embodiments, the second domain can be formed from materials such as copolymers or blends of copolymers with hydrophilic polymers such as polyvinylpyrrolidone (PVP), polyhydroxyethyl methacrylate, polyvinylalcohol, polyacrylic acid, polyethers such as polyethylene glycol, and block copolymers thereof, including, for example, di-block, tri-block, alternating, random and graft copolymers (block copolymers are discussed in U.S. Pat. Nos. 4,803,243 and 4,686,044). In one embodiment, the second domain is comprised of a silicone copolymer including a hydrophilic component, which can be formed as a unitary structure with the first domain or a separate structure adhered thereto.

The materials preferred for the second domain comprise properties such that cells cannot attach to the surface in vitro and in vivo, and that allow many molecules to freely diffuse through the membrane. Furthermore, this domain prevents cell entry or contact with device elements underlying the membrane and prevents the adherence of cells, thereby preventing the formation of a barrier cell layer. Additionally, because of the resistance of the materials to barrier cell layer formation, the membrane of the preferred embodiments is robust long-term in vivo (e.g., it does not suffer from delamination of the layers as seen in the prior art).

In some embodiments, the thickness of the cell impermeable biomaterial of the second domain (also referred to as a cell impermeable domain) is at least about a few microns in thickness. In some embodiments, the thickness of the cell impermeable domain is between about 1 micron and about 100 microns. It is noted that in some alternative embodiments thicker or thinner cell impermeable domains can be desired.

Accordingly, the characteristics of the cell impermeable membrane prevent cells from entering the membrane, but permit transport of the analyte of interest or a substance indicative of the concentration or presence of the analyte. Additionally the second domain, similar to the first domain, is constructed of biodurable materials (e.g., durable for a period of several years in vivo) that are impermeable to host cells (e.g., macrophages) such as described above.

In embodiments wherein the biointerface membrane is employed in an implantable glucose sensor, the biointerface membrane is permeable to oxygen and glucose or a substance indicative of the concentration of glucose. In embodiments wherein the membrane is employed in a drug delivery device or other device for delivering a substance to the body, the cell impermeable membrane is permeable to the drug or other substance dispensed from the device. In embodiments wherein the membrane is employed for cell transplantation, the membrane is semi-permeable, e.g., impermeable to immune cells and soluble factors responsible for rejecting transplanted tissue, but permeable to the ingress of glucose and oxygen for the purpose of sustaining the transplanted tissue; additionally, the second domain is permeable to the egress of the gene product of interest (e.g., insulin).

Interface Between Barrier Cell Disruptive Domain and Cell Impermeable Domain

The cell disruptive (first) domain and the cell impermeable (second) domain can be secured to each other by any suitable method as is known in the art. For example, the cell impermeable domain can simply be layered or cast upon the porous cell disruptive domain so as to make a mechanical attachment. Alternatively, chemical and/or mechanical attachment methods can be suitable for use. In some embodiments, chemical attachment methods can include adhesives, glues, and lamination (wherein a thermal bond is formed through the application of heat and pressure), and the like. Suitable adhesives are those capable of forming a bond with the materials that make up both the barrier cell disruptive domain and the cell impermeable domain. In one embodiment, wherein the cell disruptive domain and the cell impermeable domain comprise silicone, the materials can be designed so that they can be covalently cured to one another. In addition, an appropriate material can be designed that can be used for preparing both domains so that the composite is made in one step forming a unitary structure.

In some embodiments wherein an adhesive is employed, the adhesive can comprise a biocompatible material. However, in some embodiments adhesives not generally considered to have a high degree of biocompatibility can also be employed. Adhesives with varying degrees of biocompatibility suitable for use can include acrylates (e.g., cyanoacrylates), epoxies, methacrylates, polyurethanes, and other polymers, resins, and crosslinking agents as are known in the art.

Porous Silicone Example

Figure 6:
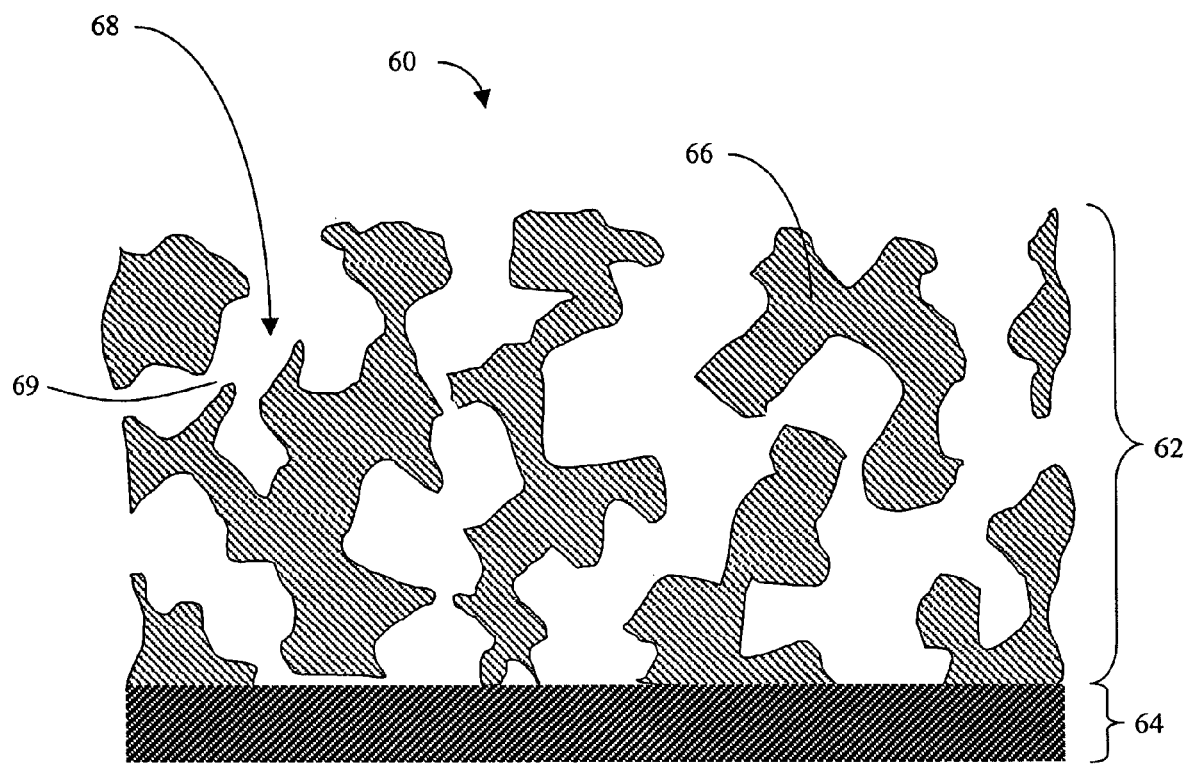
FIG. 6 is an illustration of a biointerface membrane comprising porous silicone in one embodiment.

FIG. 6 is a cross-section of a biointerface membrane 60 in one exemplary embodiment. It is noted that the first domain 62 and the second domain 64 of the membrane have characteristics such as described with reference to FIGS. 3 to 5, above. In this exemplary embodiment, the first domain of the membrane comprises silicone as described in more detail below.

The first domain 62 of the biointerface membrane comprises a silicone co-continuous solid domain 66 that contains a plurality of interconnected cavities 68 and has a depth of at least two cavities throughout a substantial portion thereof. The three-dimensional cavities are interconnected substantially throughout the first domain. Furthermore, the cavities 68 and cavity interconnections 69 can be formed in layers having different cavity dimensions. Generally, the exemplary porous silicone provides the advantages described above with reference to FIGS. 3 to 5, additionally porous silicone offers advantages for use in biointerface materials, including the mechanical robustness of the material, the ability to mold it into various structural architectures, the ability to load lipid-soluble bioactive agents into the membrane without a carrier, high oxygen solubility that allows the porous silicone to act as an oxygen antenna domain, and the ability to fill the large cavities of the material with carrier-coupled bioactive agents (e.g., collagen).

In one exemplary embodiment, first domain was formed by mixing approximately 1 kg of sugar crystals with approximately 36 grams of water for 3–6 minutes. The mixture was then pressed into a mold and baked at 80° C. for 2 hours. The silicone was vacuumed into the mold for 6 minutes and cured at 80° C. for at least 2 hours. The sugar was dissolved using heat and deionized water, resulting in a flat sheet, but porous membrane. Different architectures were obtained by varying the crystal size (e.g., crystals having an average diameter of about 90, 106, 150, 180, and 220 microns) and distribution within the mold that the silicone was cast from. After removal of silicone from the mold, the resulting membrane was measured for material thickness.

The cell-impermeable (second) domain was prepared by placing approximately 706 gm of dimethylacetamide (DMAC) into a 3L stainless steel bowl to which a polycarbonate urethane solution (1325 g, CHRONOFLEX™ AR 25% solids in DMAC and a viscosity of 5100 cp) and polyvinylpyrrolidone (125 g, PLASDONE™ K-90D) were added. The bowl was then fitted to a planetary mixer with a paddle type blade and the contents were stirred for one hour at room temperature. The cell-impermeable domain coating solution was then coated onto a PET release liner (Douglas Hansen Co., Inc. (Minneapolis, Minn.)) using a knife over roll set at a 0.012" (305 μm) gap. This film was then dried at 305° F. (152° C.). The final film was approximately 0.0015" (38 μm) thick. The biointerface membrane was prepared by pressing the porous silicone onto the cast cell-impermeable domain.

Figure 7A:
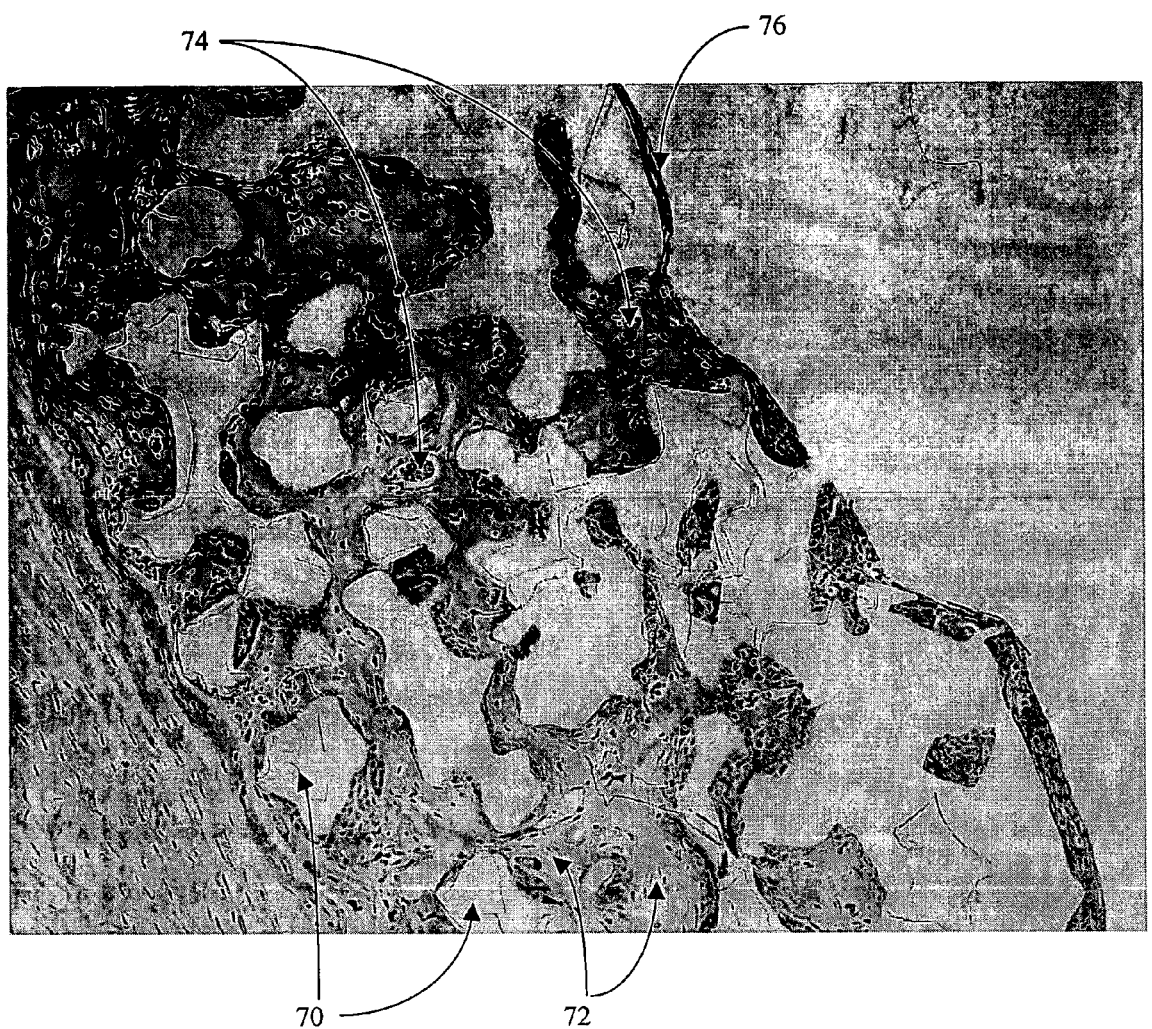
FIG. 7A is a photomicrograph at 10× magnification of a porous silicone membrane that has an approximately 90-micron nominal cavity size.
Figure 7B:
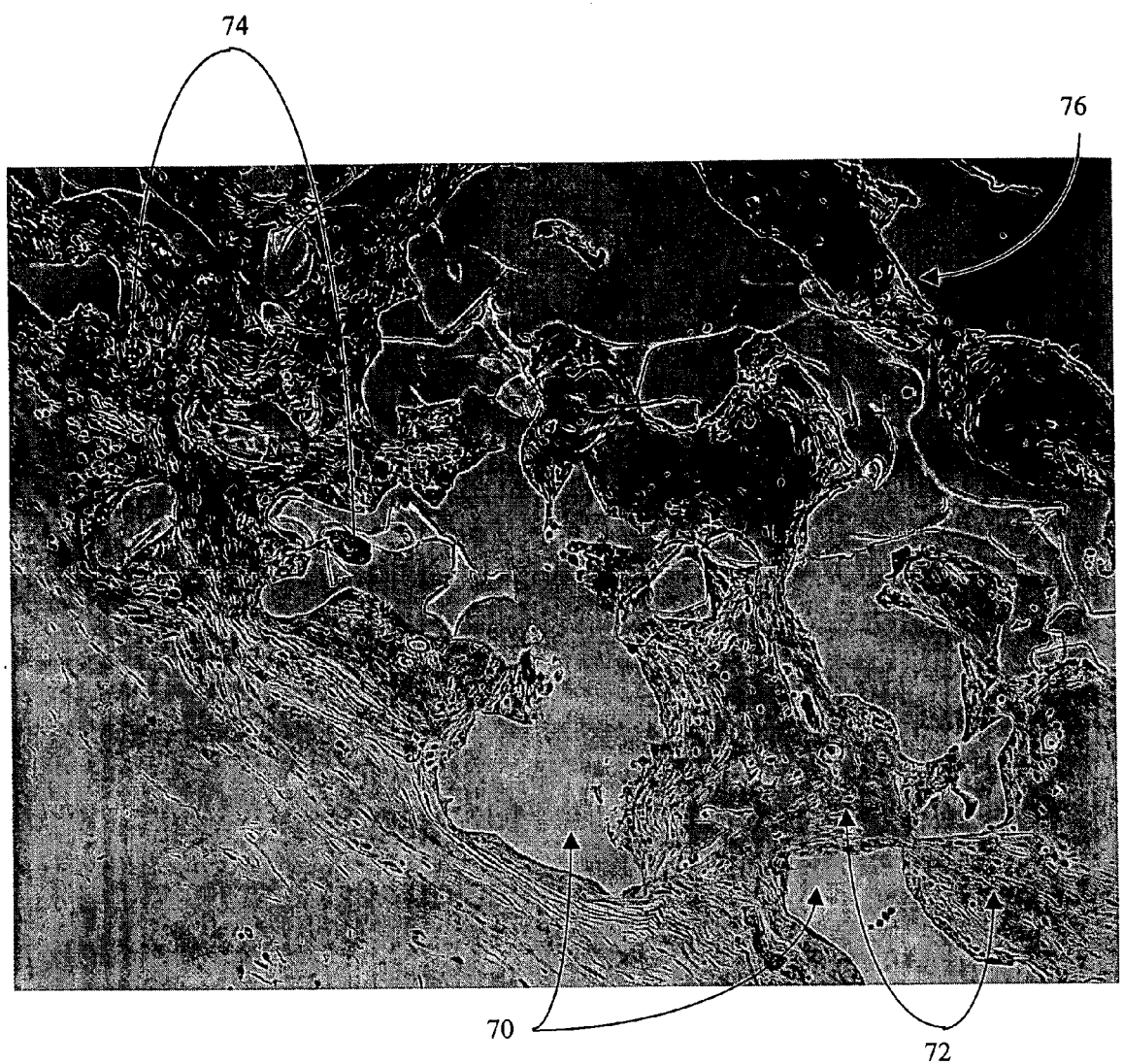
FIG. 7B is a photomicrograph at 10× magnification of a porous silicone membrane that has an approximately 220-micron nominal cavity size.

FIGS. 7A and 7B are photomicrographs that illustrate a cross-section of exemplary porous silicone membranes (formed as described in the example above) that were placed on a glucose sensor and implanted such as described in more detail with reference to FIGS. 9 and 10. After four weeks in vivo, the sensors were explanted and the porous silicone membranes were histologically processed and stained with H&E. FIG. 7A is a 10× magnification of a porous silicone membrane that has an approximately 90 micron nominal cavity size. FIG. 7B is a 10× magnification of a porous silicone membrane that has an approximately 220 micron nominal cavity size.

In the photomicrograph of the membranes of FIGS. 7A and 7B, the porous silicone 70 is infiltrated with tissue ingrowth 72 in which blood vessels 74 can be seen. Additionally, there is no obvious barrier cell layer formation at the device-tissue interface 76.

It is noted that observations from the histological slides indicate the presence of foreign body giant cells around the cavities of the first domain, which can be helpful in inducing vascularity. Furthermore, monolayers of foreign body giant cells can be seen formed in the cavities around the solid portions, however these monolayers are distinct from barrier cell layer formation because they do not block analytes (e.g., glucose) transport across the second domain (or membrane as a whole). In other words, transport of analytes can occur through the interconnectedness of the cavities through the first domain, and because there is no barrier cell layer formation, transport of analytes can continue through the second domain into a device.

Figure 8:
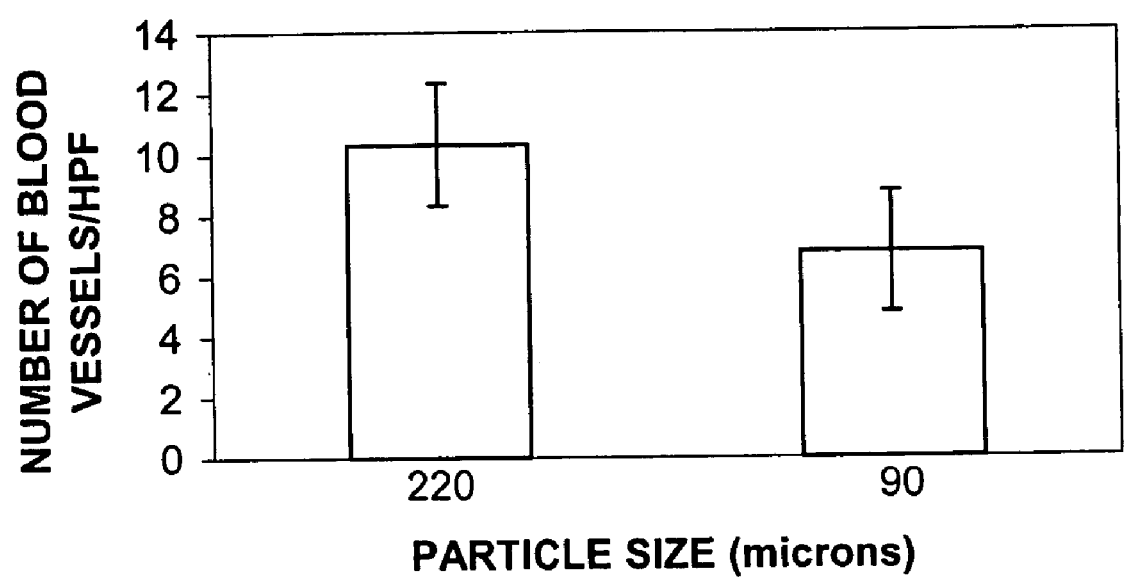
FIG. 8 is a graph that illustrates the number of blood vessels per high-powered field in vivo of the porous silicone membranes of FIGS. 7A and 7B.

FIG. 8 is a graph that shows the results of studying host responses to the porous silicone membranes of 90 and 220-micron nominal cavity size, respectively. The host response was determined by examining histological slides, such as described with reference to FIGS. 7A and 7B; that is, each sample membrane was analyzed for host response by determining the numbers of close vascular structures per high power field (CVS/HPF) comprising at least 50% of host tissue. Particularly, FIG. 8 shows number of blood vessels per high powered field (HPF) on the vertical axis and each of the porous silicone portion of the membrane having nominal cavity sizes of 90 micron and 220 micron, respectively, on the horizontal axis.

It is noted that there was no noticeable difference in the cell reaction to the implants (i.e., they were all benign) nor was there obvious scar formation at the interface between the material and host. Rather, the results showed vasculature of those membranes with nominal cavity sizes of 90 microns or greater. These data suggest that porous silicone materials with a nominal cavity size greater than or equal to 90 microns provide vascularization that is sufficient for analyte transport in certain medical device uses. These data further suggest that porous silicone containing membranes with a nominal cavity size greater than 220 microns in the first domain can result in even better vascularization in vivo, indicated by greater numbers of vessels present within the cavities of the silicone. From these results, it can be extrapolated that in some embodiments wherein the porous silicone membrane is applied as the biointerface to an implantable glucose sensor, the membrane enables sufficient diffusion of both oxygen and other substances (e.g., glucose) to the active head of the sensor.

It is noted that although one example of a biointerface membrane with silicone has been given, a variety of different materials and configurations can be successfully used for the first and/or second domains of the biointerface membrane such as described with reference to FIGS. 3 to 5, above.

Implantable Glucose Sensor Example

Figure 9A:
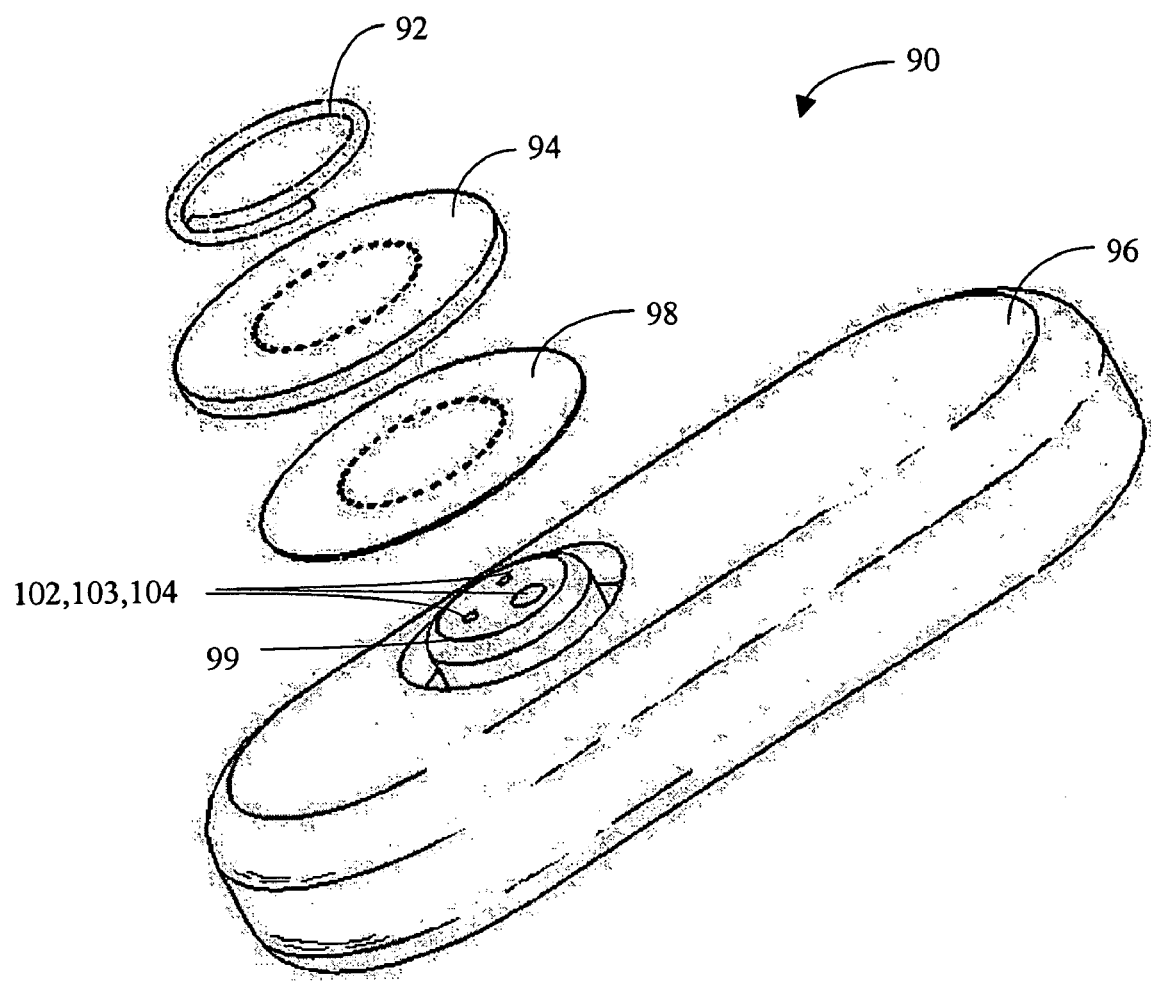
FIG. 9A is an exploded perspective view of a glucose sensor that has a biointerface membrane in one embodiment.
Figure 9B:
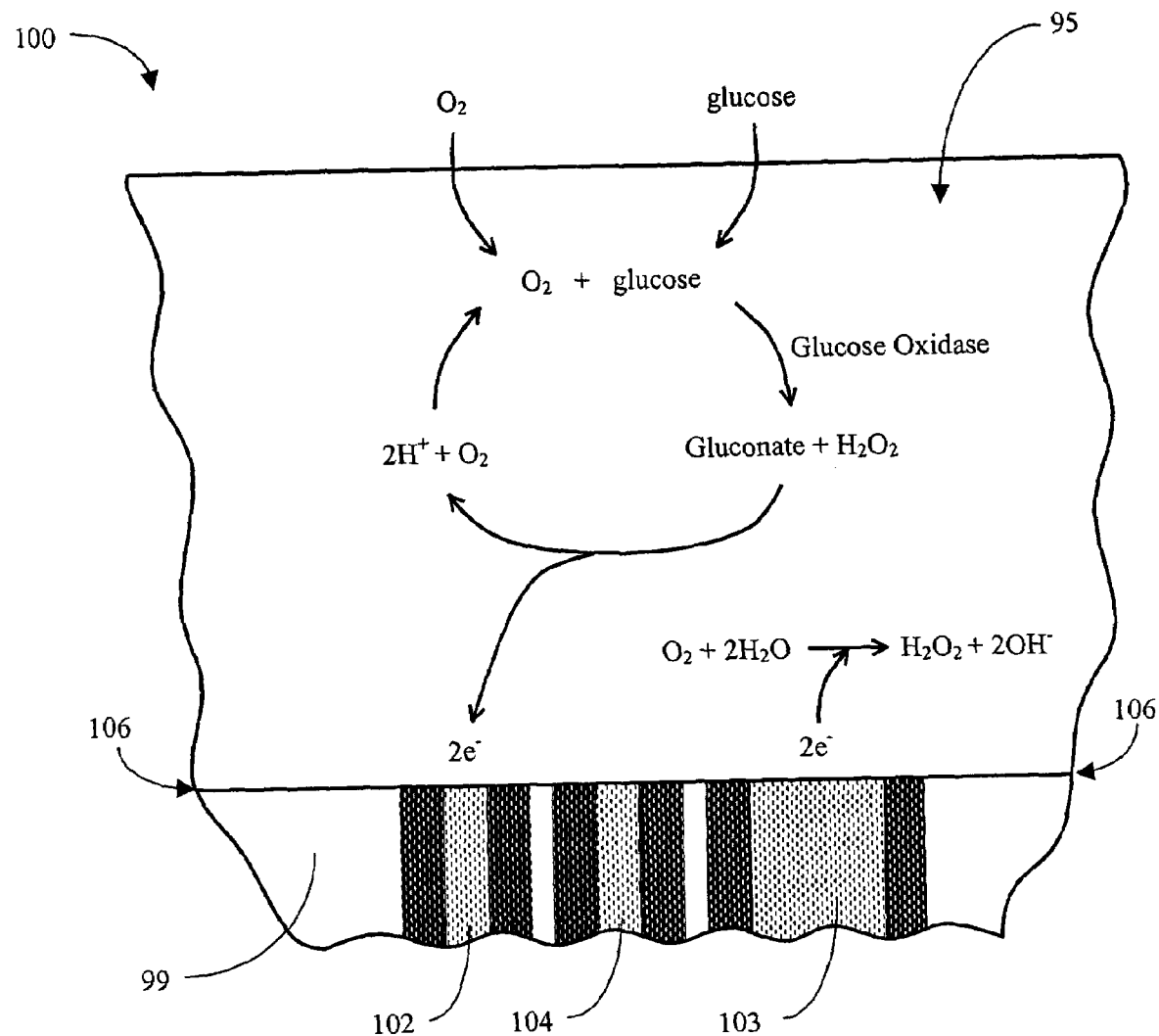
FIG. 9B is a cross-sectional cut-away view of the sensor head and membrane of FIG. 9A showing the enzymatic and electrochemical reaction that takes place within the membrane and sensor head.

FIG. 9A is an exploded view of one exemplary embodiment of an implantable glucose sensor 90 that uses a biointerface membrane 94 as described with reference to FIGS. 3 to 5, above. FIG. 9B is a cross-sectional schematic view of the sensor head and membrane of FIG. 9A showing the electrochemical reaction that takes place within the membrane and sensor head.

Although the membrane is employed in a particular glucose sensor in this example, It is noted that methods and materials of the biointerface membrane of preferred embodiments can be used with virtually any monitoring device suitable for implantation (or subject to modification allowing implantation). Suitable devices include, but are not limited to, analyte measuring devices, cell transplantation devices, drug delivery devices, electrical signal delivery and measurement devices, and other devices such as those described in U.S. Pat. Nos. 4,703,756 and 4,994,167 to Shults et al.; U.S. Pat. No. 4,703,756 to Gough et al., U.S. Pat. No. 4,431,004 to Bessman et al., and Bindra et al., Anal. Chem. 63:1692–96 (1991).

FIG. 9A illustrates an analyte-measuring device 90 that has a biointerface membrane 94 of the preferred embodiments and a sensing membrane 98. In this embodiment, a body 96 and head 99 house the electrodes (102, 103, 104) and sensor electronics that include a circuit board, a microprocessor, a battery, and an antenna (not shown). The electrodes 102, 103, 104 are, subsequently connected to the circuit board via a socket, and will be described in more detail below.

FIG. 9B is a cross-sectional cut-away view of the sensor head 99 that illustrates electrode-membrane region 100. The electrode-membrane region 100 includes a biointerface membrane 94 and a sensing membrane 98 (FIG. 9A), shown collectively as the membrane 95 that covers the sensor head 99 (FIG. 9B). Three electrodes extend through the head to the surface thereof, including a platinum working electrode 102, a platinum counter electrode 103, and a silver/silver chloride reference electrode 104, which can be affixed with epoxy or the like. The top ends of the electrodes are in contact with the electrolyte phase 106, a free-flowing fluid phase disposed between the sensing membrane and the electrodes. The sensing membrane 98 (see FIG. 9A) includes an enzyme, e.g., glucose oxidase, which covers the electrolyte phase. In turn, the biointerface membrane 94 covers the sensing membrane and serves, at least in part, to protect the sensor from external forces that can result in environmental stress cracking of the sensing membrane.

FIG. 9B additionally illustrates the amperometric electrochemical sensor technology utilized by the sensor in one embodiment. In the case of a glucose oxidase based glucose sensor, the species being measured at the working electrode is $H_2O_2$. Glucose oxidase catalyzes the conversion of oxygen and glucose to hydrogen peroxide and gluconate according to the following reaction:

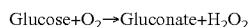

Glucose+$O_2$→Gluconate+$H_2O_2$

Because for each glucose molecule metabolized, there is a proportional change in the product $H_2O_2$, one can monitor the change in $H_2O_2$ to determine glucose concentration. Oxidation of $H_2O_2$ by the working electrode is balanced by reduction of ambient oxygen, enzyme generated $H_2O_2$, or other reducible species at the counter electrode. The counter electrode is provided to balance the current generated by the species being measured at the working electrode. It is noted that in vivo glucose concentration can vary from about one hundred times or more that of the oxygen concentration in the subcutaneous space (see Updike et al., Diabetes Care 5:207–21(1982)). Consequently, oxygen can become a limiting reactant in the electrochemical reaction if insufficient oxygen is provided to the sensor, resulting in inaccurate measurement of glucose concentration. Consequently in an implantable glucose sensor, it is advantageous to maximize the glucose (or other analyte) transport across the biointerface, such as described in more detail with reference to the biointerface membranes in FIGS. 3 to 5, above.

In this embodiment, the working electrode (anode) and counter-electrode (cathode) require oxygen in different capacities. An enzyme-containing sensing membrane that resides above an amperometric electrochemical sensor is typically employed, including an immobilized enzyme, i.e., glucose oxidase. Within the enzyme layer above the working electrode, oxygen is required for the production of $H_2O_2$ from glucose. The $H_2O_2$ produced from the glucose oxidase reaction further reacts at surface of working electrode and produces two electrons. The products of this reaction are two protons ($2H^+$), two electrons ($2e^-$), and one oxygen molecule ($O_2$) (See, e.g., Fraser, D. M. "An Introduction to In vivo Biosensing: Progress and problems." In "Biosensors and the Body," D. M. Fraser, ed., 1997, pp. 1–56 John Wiley and Sons, New York). In theory, the oxygen concentration near the working electrode, which is consumed during the glucose oxidase reaction, is replenished by the second reaction at the working electrode. Therefore, the theoretical net consumption of oxygen is zero.

Sensor Functionality of Biointerface Membranes

Figure 10A:
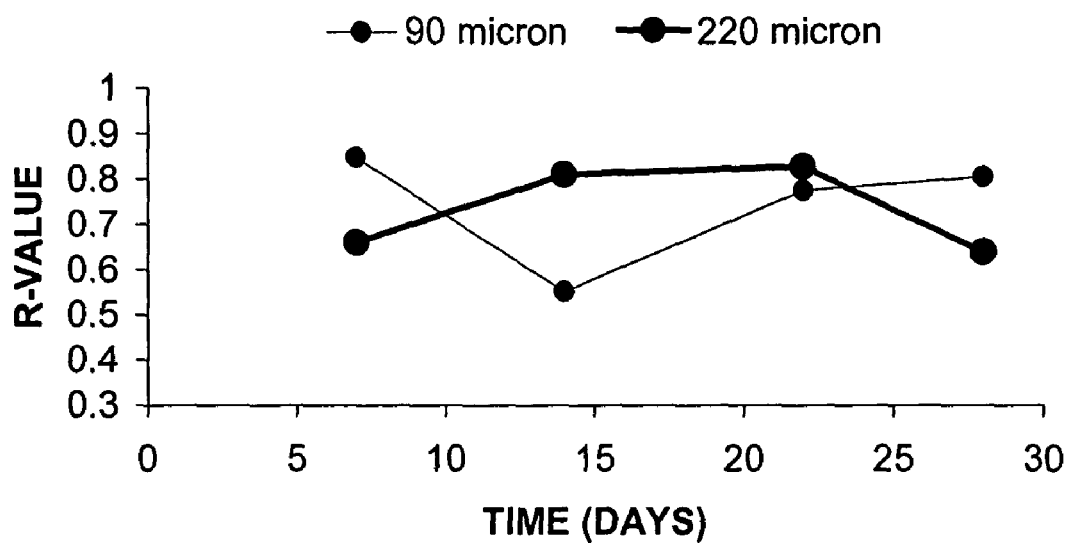
FIGS. 10A and 10B are graphs that show the results of an experiment wherein the porous silicone membranes such as described with reference to FIGS. 6 and 7 were placed on implantable glucose sensors such as described with reference to FIG. 9, and implanted in streptozocin-induced diabetic rats.
Figure 10B:
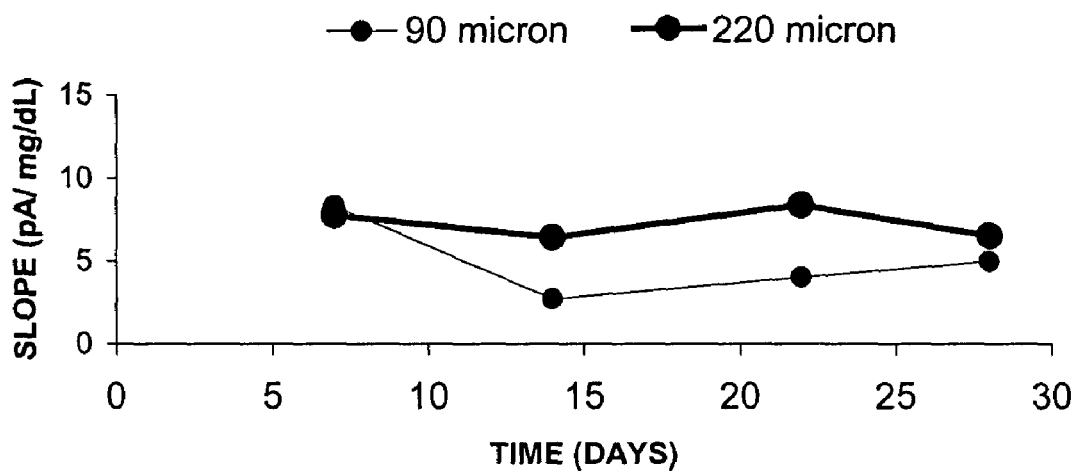

FIGS. 10A and 10B are graphs that show the results of an experiment wherein the porous silicone membranes such as described with reference to FIGS. 6 and 7 were placed on implantable glucose sensors such as described with reference to FIG. 9, and implanted in streptozocin-induced diabetic rats. Particularly, implantable glucose sensors with biointerface membranes had nominal cavity sizes of 90 microns (n=4) and 220 microns (n=4) respectively, were constructed with the described cavity sizes and implanted into subcutaneous tissue of the rats for four weeks. The data of FIGS. 10A and 10B represent days 7, 14, 21, and 28 during glucose tracking studies, which included injecting the rats with insulin to modify and monitor the glucose concentration, for the 90-micron and 220-micron groups respectively.

FIG. 10A shows the average R-values (vertical axis) for each group versus time in days (horizontal axis). R-values were obtained by correlating sensor output to the externally derived meter values, and performing a least-squares analysis. The average R-values indicate successful functionality of glucose sensors within the nominal cavity range of 90 microns and 220 microns long-term in vivo. The results indicate successful transport of glucose and oxygen across the biointerface membrane. The successful transport of those solutes can be attributed, at least in part, to the combination of vascularity within the first domain of the membrane, resistance to barrier cell formation on the second domain, and the robustness of the material, all of which are described in more detail elsewhere herein. It is noted that early R-values (e.g., first few weeks) can show lower values due to normal tissue ingrowth factors at start-up. It is also noted that variability in animal studies due to normal biological variance is known in the art and therefore is a consideration in interpretation of animal studies data.

FIG. 10B is a graph that illustrates average sensor signal strength with respect to glucose concentration (i.e., sensitivity) on the vertical axis versus time in days on the horizontal axis for the glucose tracking studies. The output can be expressed as the signal slope of the linear regression between the blood glucose values (independent value) and the sensor output (dependent value). The 220-micron biointerface sensors advantageously show consistent values over 6 pA/mg/dL and the 90-micron biointerface sensors show an expected ingrowth period (e.g., indicated by a decreased slope around day 14) and otherwise show consistent values over 4 pA/mg/dL. The overall results of this test showed excellent sensitivities in vivo. It is noted that these data, particularly the slope value maintained above a certain threshold, is an indicator of stability of the biointerface and accuracy of the sensor in vivo.

Accordingly, host response may be correlated to both function and sensitivity. The data suggest, based on the sensor output as evaluated by both R-value and slope, that the long-term success of the implantable glucose sensor enabled by the incorporation of a biointerface membrane of the preferred embodiments.

Figure 11:
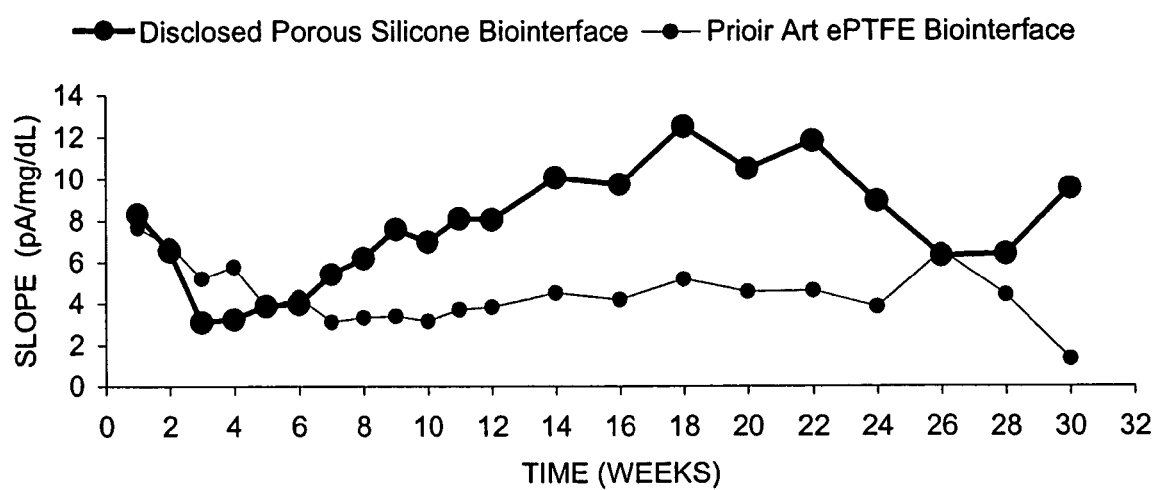
FIG. 11 is a graph that shows the results of an experiment comparing sensor function of a sensor employing a prior art ePTFE biointerface with a sensor employing a porous silicone biointerface of the preferred embodiments.

FIG. 11 is a graph that shows the results of an experiment comparing sensor function of a sensor employing a prior art biointerface with a sensor employing a membrane of the preferred embodiments. Particularly, the prior art biointerface membrane was ePTFE with pore sizes much less than the cavities of the preferred embodiments, e.g., in the range of 0.5 to 20 microns. The biointerface membrane of the preferred embodiments includes nominal cavity sizes greater than or equal to about 90 microns; however this exemplary experiment utilized a porous biointerface membrane with a nominal cavity size of about 220 microns.

The vertical axis represents sensor function expressed herein as the sensor signal strength with respect to glucose concentration (i.e., sensitivity or slope), which reflects biointerface integration in vivo. The horizontal axis represents time in weeks. It is noted that at the six-week point, the sensor functionality of the sensor with the prior art membrane is substantially similar to sensor functionality of the membrane of the preferred embodiments. At the 26-week point, the porous silicone biointerface sensor experienced a temporary, slight decline in slope, however variability in slope is expected in vivo due to normal biological and physiological factors known in the art. Calibration of the sensor provides compensation for sensitivity changes, including those sensitivity changes seen in the porous silicone biointerface sensor data of FIG. 11. Calibration of sensors is described in more detail in copending patent application Ser. No. 10/633,367 filed Aug. 1, 2003 and entitled, "SYSTEM AND METHODS FOR PROCESSiNG ANALYTE SENSOR DATA," which is incorporated herein by reference in its entirety. In contrast to the porous silicone biointerface sensor, the prior art ePTFE biointerface sensor experienced a distinct and continual decline in slope after the 26-week point, which resulted in sensitivities below the necessary (e.g., functional) threshold and therefore loss of sensor function.

The long-term trend of the membrane showed better stability implied by the consistency of the slope above the necessary threshold for proper sensor function, which indicates successful vasculature of the biointerface membrane without barrier cell layer formation, successful analyte transport across the membrane, and mechanical stability of the membrane in vivo. Unfortunately, the prior art membrane experienced an eventual decline below a necessary threshold for proper sensor function, particularly after week 26. It has been observed through these data and histological examination that the ePTFE biointerface sensor functionality declines long term in vivo due to cellular invasion and damage to the three-dimensional structure of the membrane (e.g., which results in barrier cell layer formation); particularly, the fine fibers of the ePTFE material long term in vivo exhibit weakness resulting in structural degradation and delamination of the biointerface from the adjacent membrane structure and/or sensor as a whole.

The above description discloses several methods' and materials of the disclosed invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims. All patents, applications, and other references cited herein are hereby incorporated by reference in their entirety.

What is claimed is:

1. A biointerface membrane suitable for implantation in a soft tissue of an animal, the membrane comprises:
   a first domain, wherein the first domain supports tissue ingrowth and interferes with barrier cell layer formation, wherein the first domain comprises an open cell configuration having a plurality of interconnected cavities and a solid portion, and wherein a substantial number of the interconnected cavities are greater than or equal to about 90 microns in at least one dimension; and
   a second domain, wherein the second domain allows passage of an analyte, and wherein the second domain is resistant to cellular attachment and is impermeable to cells and cell processes.

2. The biointerface membrane according to claim 1, wherein the first domain comprises a depth of greater than one cavity in three dimensions substantially throughout an entirety of the first domain.

3. The biointerface membrane according to claim 1, wherein the cavities and a plurality of cavity interconnections are formed in a plurality of layers having different cavity dimensions.

4. The biointerface membrane according to claim 1, wherein a substantial number of the cavities are greater than or equal to about 160 microns in at least one dimension.

5. The biointerface membrane according to claim 1, wherein a substantial number of the cavities are greater than or equal to about 220 microns in at least one dimension.

6. The biointerface membrane according to claim 1, wherein a substantial number of the cavities are greater than or equal to about 285 microns in at least one dimension.

7. The biointerface membrane according to claim 1, wherein a substantial number of the cavities are greater than or equal to about 350 microns in at least one dimension.

8. The biointerface membrane according to claim 1, wherein a substantial number of the cavities are greater than or equal to about 370 microns in at least one dimension.

9. The biointerface membrane according to claim 1, wherein a substantial number of the cavities are from about 90 microns to about 370 microns in at least one dimension.

10. The biointerface membrane according to claim 1, wherein a substantial number of the cavities are from about 220 microns to about 350 microns in at least one dimension.

11. The biointerface membrane according to claim 1, wherein a substantial number of the cavities are from about 220 microns to about 285 microns in at least one dimension.

12. The biointerface membrane according to claim 1, wherein a substantial number of the cavities are less than or equal to about 1000 microns in a longest dimension.

13. The biointerface membrane according to claim 1, wherein a substantial number of the cavities are less than or equal to about 500 microns in a longest dimension.

14. The biointerface membrane according to claim 1, wherein a substantial number of shortest dimensions of the solid portion are greater than or equal to about 5 microns and wherein a substantial number of longest dimensions of the solid portion are greater than or equal to about 2000 microns.

15. The biointerface membrane according to claim 1, wherein a substantial number of shortest dimensions of the solid portion are greater than or equal to about 10 microns and wherein a substantial number of longest dimensions of the solid portion are greater than or equal to about 1000 microns.

16. The biointerface membrane according to claim 1, wherein a substantial number of shortest dimensions of the solid portion are greater than or equal to about 10 microns and wherein a substantial number of longest dimensions of the solid portion are greater than or equal to about 400 microns.

17. The biointerface membrane according to claim 1, wherein the solid portion comprises silicone.

18. The biointerface membrane according to claim 1, wherein the solid portion comprises polyurethane.

19. The biointerface membrane according to claim 1, wherein the solid portion comprises a block copolymer.

20. The biointerface membrane according to claim 1, wherein the solid portion comprises a material selected from the group consisting of polytetrafluoroethylene, polyethylene-co-tetrafluoroethylene, polyolefin, polyester, and polycarbonate.

21. The biointerface membrane according to claim 1, wherein the second domain comprises a biostable material.

22. The biointerface membrane according to claim 21, wherein the biostable material comprises polyurethane and a hydrophilic polymer.

23. The biointerface membrane according to claim 21, wherein the biostable material comprises polyurethane and polyvinylpyrrolidone.

24. The biointerface membrane according to claim 1, wherein the second domain comprises greater than or equal to about 5 wt. % polyurethane and greater than or equal to about 45 wt. % polyvinylpyrrolidone.

25. The biointerface membrane according to claim 24, wherein the second domain comprises greater than or equal to about 20 wt. % polyurethane and greater than or equal to about 35 wt. % polyvinylpyrrolidone.

26. The biointerface membrane according to claim 25, wherein the second domain comprises polyurethane and about 27 wt. % polyvinylpyrrolidone.

27. The biointerface membrane according to claim 1, wherein the second domain comprises a silicone copolymer.

28. The biointerface membrane according to claim 1, wherein the analyte comprises glucose.

* * * * *

(12) EX PARTE REEXAMINATION CERTIFICATE (8447th)
United States Patent
Brauker et al.

(10) Number: US 7,192,450 C1
(45) Certificate Issued: Aug. 2, 2011

(54) POROUS MEMBRANES FOR USE WITH IMPLANTABLE DEVICES

(75) Inventors: James H. Brauker, San Diego, CA (US); Victoria Carr-Brendel, Pleasanton, CA (US); Mark A. Tapsak, Orangeville, PA (US)

(73) Assignee: DexCom, Inc., San Diego, CA (US)

Reexamination Request:
No. 90/011,330, Nov. 12, 2010

Reexamination Certificate for:
| | |
|---|---|
| Patent No.: | 7,192,450 |
| Issued: | Mar. 20, 2007 |
| Appl. No.: | 10/647,065 |
| Filed: | Aug. 22, 2003 |

Related U.S. Application Data

(60) Provisional application No. 60/472,673, filed on May 21, 2003.

(51) Int. Cl.
*A61F 2/02* (2006.01)

(52) U.S. Cl. .................................. 623/23.76
(58) Field of Classification Search .............. 623/23
See application file for complete search history.

(56) References Cited

U.S. PATENT DOCUMENTS

| | | | |
|---|---|---|---|
| 3,957,651 | A | 5/1976 | Kesting |
| 5,382,514 | A | 1/1995 | Passaniti et al. |
| 5,706,807 | A | 1/1998 | Picha |
| 5,858,365 | A | 1/1999 | Faller |
| 7,404,819 | B1 | 7/2008 | Darios et al. |
| 2001/0044413 | A1 | 11/2001 | Pierce et al. |
| 2001/0053933 | A1 | 12/2001 | Phaneuf et al. |
| 2002/0019330 | A1 | 2/2002 | Murray et al. |
| 2005/0031689 | A1 | 2/2005 | Shults et al. |
| 2006/0198864 | A1 | 9/2006 | Shults et al. |
| 2006/0204536 | A1 | 9/2006 | Shults et al. |
| 2010/0256779 | A1 | 10/2010 | Brauker et al. |

FOREIGN PATENT DOCUMENTS

WO  WO00/13003  3/2000

OTHER PUBLICATIONS

Answers.com, "xenogenic." The American Heritage Stedman's Medical Dictionary. Houghton Mifflin Company, 2002. Answers.com Nov. 7, 2006 http://www.Answers.com/topic/xenogenic.
Ladd et al., Structure Determination by X-ray Crystallography, 3rd ed. Plenum, 1996, Ch. 1, pp. xxi–xxiv and 1–58.
Panetti 2002. Differential effects of sphingosine 1-phosphate and lysophosphatidic acid on endothelial cells. Biochimica et Biophysica Acta 1582:190–196.
Sharkawy et al. 1996. Engineering the tissue which encapsulates subcutaneous implants. I. Diffusion properties, J Biomed Mater Res, 37:401–412.
Zhang et al. 1994. Elimination of the acetaminophen interference in an implantable glucose sensor. Analytical Chemistry 66(7):1183–1188.

*Primary Examiner* — Jeanne M Clark

(57) ABSTRACT

A membrane for implantation in soft tissue comprising a first domain that supports tissue ingrowth, disrupts contractile forces typically found in a foreign body response, encourages vascularity, and interferes with barrier cell layer formation, and a second domain that is resistant to cellular attachment, is impermeable to cells and cell processes, and allows the passage of analytes. The membrane allows for long-term analyte transport in vivo and is suitable for use as a biointerface for implantable analyte sensors, cell transplantation devices, drug delivery devices, and/or electrical signal delivering or measuring devices. The membrane architecture, including cavity size, depth, and interconnectivity, provide long-term robust functionality of the membrane in vivo.

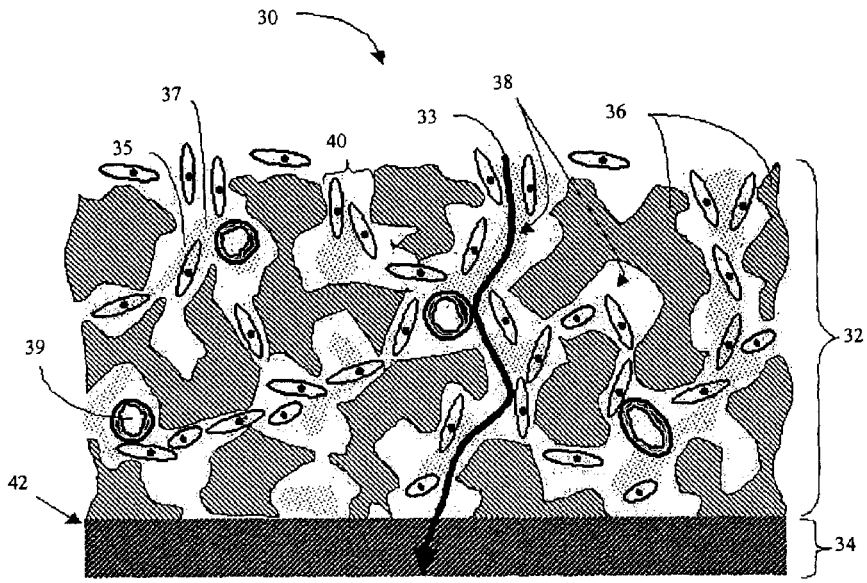

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1, 2, 4-13, 17, 18 and 28 is confirmed.

New claim 29 is added and determined to be patentable.

Claims 3, 14-16, and 19-27 were not reexamined.

*29. A biointerface membrane according to claim 1, further comprising an enzyme membrane, wherein the enzyme membrane comprises an enzyme configured to react with glucose.*

\* \* \* \* \*